US011059890B2

(12) United States Patent
Li et al.

(10) Patent No.: US 11,059,890 B2
(45) Date of Patent: Jul. 13, 2021

(54) ANTI-HUMAN PD-1 HUMANIZED MONOCLONAL ANTIBODY AND APPLICATION THEREOF

(71) Applicant: REYOUNG (SUZHOU) BIOLOGY SCIENCE & TECHNOLOGY CO., LTD, Jiangsu (CN)

(72) Inventors: Ge Li, Jiangsu (CN); Shuhua Guo, Jiangsu (CN); Jiachun Zhang, Jiangsu (CN); Yixiang Zhu, Jiangsu (CN)

(73) Assignee: REYOUNG (SUZHOU) BIOLOGY SCIENCE & TECHNOLOGY CO., LTD, Suzhou (CN)

( * ) Notice: Subject to any disclaimer, the term of this patent is extended or adjusted under 35 U.S.C. 154(b) by 223 days.

(21) Appl. No.: 16/084,726

(22) PCT Filed: Jun. 3, 2016

(86) PCT No.: PCT/CN2016/084644
§ 371 (c)(1),
(2) Date: Sep. 13, 2018

(87) PCT Pub. No.: WO2017/201766
PCT Pub. Date: Nov. 30, 2017

(65) Prior Publication Data
US 2019/0071501 A1 Mar. 7, 2019

(30) Foreign Application Priority Data

May 24, 2016 (CN) .......................... 201610345750.1

(51) Int. Cl.
*C07K 16/28* (2006.01)
*A61K 47/68* (2017.01)
*A61K 39/395* (2006.01)

(52) U.S. Cl.
CPC ...... *C07K 16/2818* (2013.01); *A61K 39/3955* (2013.01); *A61K 47/6849* (2017.08); *C07K 2317/24* (2013.01); *C07K 2317/30* (2013.01); *C07K 2317/56* (2013.01); *C07K 2317/565* (2013.01); *C07K 2317/567* (2013.01); *C07K 2317/76* (2013.01); *C07K 2317/92* (2013.01); *C07K 2317/94* (2013.01); *C07K 2319/30* (2013.01)

(58) Field of Classification Search
None
See application file for complete search history.

(56) References Cited

U.S. PATENT DOCUMENTS

2006/0034826 A1* 2/2006 Carreno ................. A61P 37/06
424/130.1
2014/0044738 A1 2/2014 Langermann et al.
2015/0274835 A1 10/2015 Marasco et al.
2016/0108123 A1 4/2016 Freeman et al.

FOREIGN PATENT DOCUMENTS

| CN | 1753912 A | 3/2006 |
| CN | 101213297 A | 7/2008 |
| CN | 102131828 A | 7/2011 |
| CN | 104250302 A | 12/2014 |
| CN | 105175544 A | 12/2015 |
| WO | 2011110604 A1 | 9/2011 |
| WO | 2015035606 A1 | 3/2015 |
| WO | 2015085847 A1 | 6/2015 |
| WO | 2016022630 A1 | 2/2016 |

OTHER PUBLICATIONS

Mariuzza (Annu. Rev. Biophys. Biophys. Chem., 16: 139-159, 1987).*
Chothia C, Lesk A M, Tramontano A, et al. Conformations of immunoglobulin hypervariable regions[J]. Nature, 1989, 342(6252):877-883.
Chothia C, Lesk A M. Canonical structures for the hypervariable regions of immunoglobulins.[J]. Journal of Molecular Biology, 1987, 196(4):901-917.
International Search Report & Written Opinion dated Feb. 14, 2017 from PCT Application No. PCT/CN2016/084643.
International Search Report & Written Opinion from PCT Application No. PCT/CN2016/084644.

* cited by examiner

*Primary Examiner* — Nelson B Moseley, II
(74) *Attorney, Agent, or Firm* — Innovation Capital Law Group, LLP; Vic Lin

(57) ABSTRACT

The present invention relates to the biomedicine field, in particular to an anti-human PD-1 humanized monoclonal antibody and its applications. The invention obtains an anti-human PD-1 humanized monoclonal antibody with good specificity, high affinity and stability by screening, and the antibody can specifically bind to human PD-1 instead of binding to other members of CD28 family, block the binding of PD-L1 and PD-1 with CD80 and partially restore functions of T-cells, so it can significantly inhibit the growth of tumor.

25 Claims, 6 Drawing Sheets

Specification includes a Sequence Listing.

SEQUENCE LISTING

```
<160> NUMBER OF SEQ ID NOS: 45

<210> SEQ ID NO 1
<211> LENGTH: 357
<212> TYPE: DNA
<213> ORGANISM: Artificial Sequence
<220> FEATURE:
<223> OTHER INFORMATION: Synthesized

<400> SEQUENCE: 1
gacgtgaagc tggtggagtc tgggggaggc ttagtgaagc ctggagggtc cctgaaactc      60
tcctgtgcag cctctggatt cactttcagt agctatacca tgtcttgggt tcgccagact     120
ccggagaaga ggctggagtg ggtcgcaacc attagtaatg gtggtagttt cacctactat     180
ccagacagta tgaagggccg attccaccat tccagadaca atgccaagaa cacctgtac     240 ctgcaaatga gcagtctgaa gtctgaggac acagccatgt attactgtac aagagattct     300
gattactacg gtatctttga ctactggggc caaggcacca ctctcacagt ctcctca       357

<210> SEQ ID NO 2
<211> LENGTH: 119
<212> TYPE: PRT
<213> ORGANISM: Artificial Sequence
<220> FEATURE:
<223> OTHER INFORMATION: Synthesized

<400> SEQUENCE: 2
```

Asp Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Thr Met Ser Trp Val Arg Gln Thr Pro Glu Lys Arg Leu Glu Trp Val
        35                  40                  45

Ala Thr Ile Ser Asn Gly Gly Ser Phe Thr Tyr Tyr Pro Asp Ser Met
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
            85                  90                  95

Thr Arg Asp Ser Asp Tyr Tyr Gly Ile Phe Asp Tyr Trp Gly Gln Gly
            100                 105                 110

Thr Thr Leu Thr Val Ser Ser
            115

<210> SEQ ID NO 3
<211> LENGTH: 339
<212> TYPE: DNA
<213> ORGANISM: Artificial Sequence
<220> FEATURE:
<223> OTHER INFORMATION: Synthesized

<400> SEQUENCE: 3
gatattgtga taacccagga tgaactctcc aatcctgtca cttctggaga atcagtttcc      60
atctcctgca ggtctagtaa gagtctccta tataaggatg gaagacata cttgaattgg     120 tttctgcaga gaccaggaca atctcctcag ctcctgatct atttgatgtc cacccgtgca    180
tcaggagtct cagaccggtt tagtggcagt gggtcaggaa cagatttcac cctggaaatc    240
agtagagtga aggctgagga tgtgggtgtt tattactgtc aacaacttgt agaggatcca    300
ttcacgttcg gctcggggac aaagttggaa ataaaacgg                            339

<210> SEQ ID NO 4
<211> LENGTH: 113
<212> TYPE: PRT
<213> ORGANISM: Artificial Sequence
<220> FEATURE:
<223> OTHER INFORMATION: Synthesized

<400> SEQUENCE: 4

Asp Ile Val Ile Thr Gln Asp Glu Leu Ser Asn Pro Val Thr Ser Gly
1               5                   10                  15

Glu Ser Val Ser Ile Ser Cys Arg Ser Ser Lys Ser Leu Leu Tyr Lys
            20                  25                  30

Asp Gly Lys Thr Tyr Leu Asn Trp Phe Leu Gln Arg Pro Gly Gln Ser
        35                  40                  45

Pro Gln Leu Leu Ile Tyr Leu Met Ser Thr Arg Ala Ser Gly Val Ser
    50                  55                  60

Asp Arg Phe Ser Gly Ser Gly Ser Gly Thr Asp Phe Thr Leu Glu Ile
65                  70                  75                  80

Ser Arg Val Lys Ala Glu Asp Val Gly Val Tyr Tyr Cys Gln Gln Leu
            85                  90                  95

Val Glu Asp Pro Phe Thr Phe Gly Ser Gly Thr Lys Leu Glu Ile Lys
            100                 105                 110

Arg

<210> SEQ ID NO 5
<211> LENGTH: 357
<212> TYPE: DNA
<213> ORGANISM: Artificial Sequence
<220> FEATURE:
<223> OTHER INFORMATION: Synthesized

<400> SEQUENCE: 5

```
gaggtgcaac tggtggaaag cggcggagga ctggtgaagc ccggaggatc cctgaggctg    60
tcctgtgccg cctccggctt caccttcagc agctacacca tgtcctgggt gaggcaggct   120
cccggaaagg gcctggagtg gtggctacc atcagcaacg gaggctcctt cacctattac    180
cctgactcca tgaagggcag gttcacaatc tcccgggaca actccaagaa caccctgtac   240
ctgcagatgt ccagcctgag ggctgaggac accgccgtgt attactgcgc cagggacagc   300
gactattacg gcatcttcga ctactggggc cagggaacaa ccgtgacagt gagctcc      357
```

<210> SEQ ID NO 6
<211> LENGTH: 340
<212> TYPE: DNA
<213> ORGANISM: Artificial Sequence
<220> FEATURE:
<223> OTHER INFORMATION: Synthesized

<400> SEQUENCE: 6

```
cgacatcgtg atgacccagt cccctctgtc cctgcctgtg acacccggag agcctgcctc    60
catcagctgc aggagctcca gagcctgct gtacaaagac ggcaagacct acctgaactg   120
gtatttacag aagcctggcc agtcccccca gctgctgatc tacctcatgt ccaccagggc   180
ctccggagtg cctgatcggt tcagcggatc cggcagcggc accgatttca ccctcaagat   240
ctccagggtg gaggccgagg acgtgggagt gtactattgc cagcagctgg tggaggaccc   300
cttcaccttc ggccaaggca aaagctgga gatcaagagg                          340
```

<210> SEQ ID NO 7
<211> LENGTH: 1407
<212> TYPE: DNA
<213> ORGANISM: Artificial Sequence
<220> FEATURE:
<223> OTHER INFORMATION: Synthesized

<400> SEQUENCE: 7

```
gccaccatgt acaggatgca actcctgtct tgcattgcac taagtcttgc acttgtcacg    60
aattcggagg tgcaactggt ggaaagcggc ggaggactgg tgaagcccgg aggatccctg   120
aggctgtcct gtgccgcctc cggcttcacc ttcagcagct acaccatgtc ctgggtgagg   180
caggctcccg gaaagggcct ggagtgggtg ctaccatca gcaacggagg ctccttcacc    240
tattaccctg actccatgaa gggcaggttc acaatctccc gggacaactc caagaacacc   300
ctgtacctgc agatgtccag cctgagggct gaggacaccg ccgtgtatta ctgcgccagg   360
gacagcgact attacggcat cttcgactac tggggccagg gaacaaccgt gacagtgagc   420
tccgctagca caaaaggccc ctccgtgttt cccctggctc ctgttccag gagcaccagc    480 gaatccacag ctgccctcgg ctgcctggtc aaggattact ccccgagcc cgtgaccgtc   540 agctggaact ccggagccct gacatccggc gtccacacct ttcctgctgt gctgcagagc   600
tccggcctgt acagcctctc cagcgtcgtc acagtccct ccagctccct cggcaccaag    660
acctatacct gcaacgtcga ccacaagccc agcaacacca aggtggacaa gagggtggag   720
agcaagtacg gacctccttg tcccccctgt cctgctcctg agtttctcgg cggccccttcc   780
```

```
gtctttctct tccccccaa acccaaggac accctgatga tcagcaggac acccgaggtc    840
acctgtgtcg tcgtcgacgt ctcccaggaa gaccccgagg tgcagttcaa ttggtatgtg    900
gacggcgtgg aggtgcacaa cgccaagacc aaacccaggg aggagcagtt taacagcacc    960
tacagggtgg tgagcgtgct gacagtcctg caccaggact ggctcaacgg caaggagtac   1020
aagtgcaagg tgagcaataa gggactcccc agcagcatcg agaaaaccat cagcaaggcc   1080
aaaggccagc ccagagagcc ccaggtgtac acactgcctc ctagccagga ggagatgaca   1140
aagaaccagg tgagcctgac ctgtctggtg aagggattct accccagcga tattgccgtg   1200
gaatgggagt ccaacggcca acccgagaat aactacaaga ccaccctcc tgtcctggat    1260 agcgacggca gcttctttct gtactccaga ctgaccgtgg ataagagcag gtggcaggag   1320
ggaaacgtct tcagctgtag cgtcatgcac gaggccctgc acaaccacta cacccagaag   1380
agcctgtccc tgtccctcgg aaaatga                                       1407

<210> SEQ ID NO 8
<211> LENGTH: 446
<212> TYPE: PRT
<213> ORGANISM: Artificial Sequence
<220> FEATURE:
<223> OTHER INFORMATION: Synthesized

<400> SEQUENCE: 8

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Lys Gly Leu Glu Trp Val
        35                  40                  45

Ala Thr Ile Ser Asn Gly Gly Ser Phe Thr Tyr Tyr Pro Asp Ser Met
    50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Arg Asp Ser Asp Tyr Tyr Gly Ile Phe Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
```

245                 250                 255
Glu Val Thr Cys Val Val Val Asp Val Ser Gln Glu Asp Pro Glu Val
                260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Tyr Arg Val Val Ser Val
        290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
        435                 440                 445

<210> SEQ ID NO 9
<211> LENGTH: 24
<212> TYPE: DNA
<213> ORGANISM: Artificial Sequence
<220> FEATURE:
<223> OTHER INFORMATION: Synthesized

<400> SEQUENCE: 9
ggcttcacct tcagcagcta cacc                                           24

<210> SEQ ID NO 10
<211> LENGTH: 24
<212> TYPE: DNA
<213> ORGANISM: Artificial Sequence
<220> FEATURE:
<223> OTHER INFORMATION: Synthesized

<400> SEQUENCE: 10
atcagcaacg gaggctcctt cacc                                           24

<210> SEQ ID NO 11
<211> LENGTH: 36
<212> TYPE: DNA
<213> ORGANISM: Artificial Sequence
<220> FEATURE:
<223> OTHER INFORMATION: Synthesized

<400> SEQUENCE: 11
gccagggaca gcgactatta cggcatcttc gactac                              36

<210> SEQ ID NO 12
<211> LENGTH: 75
<212> TYPE: DNA
<213> ORGANISM: Artificial Sequence

```
<220> FEATURE:
<223> OTHER INFORMATION: Synthesized

<400> SEQUENCE: 12
gaggtgcaac tggtggaaag cggcggagga ctggtgaagc ccggaggatc cctgaggctg    60
tcctgtgccg cctcc                                                    75

<210> SEQ ID NO 13
<211> LENGTH: 51
<212> TYPE: DNA
<213> ORGANISM: Artificial Sequence
<220> FEATURE:
<223> OTHER INFORMATION: Synthesized

<400> SEQUENCE: 13
atgtcctggg tgaggcaggc tcccggaaag ggcctggagt gggtggctac c             51

<210> SEQ ID NO 14
<211> LENGTH: 114
<212> TYPE: DNA
<213> ORGANISM: Artificial Sequence
<220> FEATURE:
<223> OTHER INFORMATION: Synthesized

<400> SEQUENCE: 14
tattaccctg actccatgaa gggcaggttc acaatctccc gggacaactc caagaacacc    60
ctgtacctgc agatgtccag cctgagggct gaggacaccg ccgtgtatta ctgc         114

<210> SEQ ID NO 15
<211> LENGTH: 33
<212> TYPE: DNA
<213> ORGANISM: Artificial Sequence
<220> FEATURE:
<223> OTHER INFORMATION: Synthesized

<400> SEQUENCE: 15
tggggccagg gaacaaccgt gacagtgagc tcc                                 33

<210> SEQ ID NO 16
<211> LENGTH: 119
<212> TYPE: PRT
<213> ORGANISM: Artificial Sequence
<220> FEATURE:
<223> OTHER INFORMATION: Synthesized

<400> SEQUENCE: 16

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Thr Met Ser Trp Val Arg Gln Ala Pro Gly Lys Gly Leu Glu Trp Val
        35                  40                  45

Ala Thr Ile Ser Asn Gly Gly Ser Phe Thr Tyr Tyr Pro Asp Ser Met
    50                  55                  60

Lys Gly Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Val Tyr Tyr Cys
                85                  90                  95

Ala Arg Asp Ser Asp Tyr Tyr Gly Ile Phe Asp Tyr Trp Gly Gln Gly
            100                 105                 110

Thr Thr Val Thr Val Ser Ser
```

```
<210> SEQ ID NO 17
<211> LENGTH: 8
<212> TYPE: PRT
<213> ORGANISM: Artificial Sequence
<220> FEATURE:
<223> OTHER INFORMATION: Synthesized

<400> SEQUENCE: 17

Gly Phe Thr Phe Ser Ser Tyr Thr
1               5

<210> SEQ ID NO 18
<211> LENGTH: 8
<212> TYPE: PRT
<213> ORGANISM: Artificial Sequence
<220> FEATURE:
<223> OTHER INFORMATION: Synthesized

<400> SEQUENCE: 18

Ile Ser Asn Gly Gly Ser Phe Thr
1               5

<210> SEQ ID NO 19
<211> LENGTH: 12
<212> TYPE: PRT
<213> ORGANISM: Artificial Sequence
<220> FEATURE:
<223> OTHER INFORMATION: Synthesized

<400> SEQUENCE: 19

Ala Arg Asp Ser Asp Tyr Tyr Gly Ile Phe Asp Tyr
1               5                   10

<210> SEQ ID NO 20
<211> LENGTH: 25
<212> TYPE: PRT
<213> ORGANISM: Artificial Sequence
<220> FEATURE:
<223> OTHER INFORMATION: Synthesized

<400> SEQUENCE: 20

Glu Val Gln Leu Val Glu Ser Gly Gly Gly Leu Val Lys Pro Gly Gly
1               5                   10                  15

Ser Leu Arg Leu Ser Cys Ala Ala Ser
            20                  25

<210> SEQ ID NO 21
<211> LENGTH: 17
<212> TYPE: PRT
<213> ORGANISM: Artificial Sequence
<220> FEATURE:
<223> OTHER INFORMATION: Synthesized

<400> SEQUENCE: 21

Met Ser Trp Val Arg Gln Ala Pro Gly Lys Gly Leu Glu Trp Val Ala
1               5                   10                  15

Thr

<210> SEQ ID NO 22
<211> LENGTH: 38
<212> TYPE: PRT
<213> ORGANISM: Artificial Sequence
<220> FEATURE:
<223> OTHER INFORMATION: Synthesized
```

<400> SEQUENCE: 22

Tyr Tyr Pro Asp Ser Met Lys Gly Arg Phe Thr Ile Ser Arg Asp Asn
1               5                   10                  15

Ser Lys Asn Thr Leu Tyr Leu Gln Met Ser Ser Leu Arg Ala Glu Asp
            20                  25                  30

Thr Ala Val Tyr Tyr Cys
        35

<210> SEQ ID NO 23
<211> LENGTH: 11
<212> TYPE: PRT
<213> ORGANISM: Artificial Sequence
<220> FEATURE:
<223> OTHER INFORMATION: Synthesized

<400> SEQUENCE: 23

Trp Gly Gln Gly Thr Thr Val Thr Val Ser Ser
1               5                   10

<210> SEQ ID NO 24
<211> LENGTH: 726
<212> TYPE: DNA
<213> ORGANISM: Artificial Sequence
<220> FEATURE:
<223> OTHER INFORMATION: Synthesized

<400> SEQUENCE: 24
gccaccatgt acaggatgca actcctgtct tgcattgcac taagtcttgc acttgtcacg      60
aattcggaca tcgtgatgac ccagtcccct ctgtccctgc ctgtgacacc cggagagcct    120
gcctccatca gctgcaggag ctccaagagc ctgctgtaca agacggcaa gacctacctg     180
aactggtatt tacagaagcc tggccagtcc ccccagctgc tgatctacct catgtccacc    240
agggcctccg gagtgcctga tcggttcagc ggatccggca gcggcaccga tttcaccctc    300
aagatctcca gggtggaggc cgaggacgtg ggagtgtact attgccagca gctggtggag    360
gaccccttca ccttcggcca aggcacaaag ctggagatca agaggactgt ggctgcacca    420
tctgtcttca tcttcccgcc atctgatgag cagttgaaat ctggaactgc ctctgttgtg    480
tgcctgctga ataacttcta tcccagagag gccaaagtac agtggaaggt ggataacgcc    540
ctccaatcgg gtaactccca ggagagtgtc acagagcagg acagcaagga cagcacctac    600
agcctcagca gcaccctgac gctgagcaaa gcagactacg agaaacacaa agtctacgcc    660
tgcgaagtca cccatcaggg cctgagctcg cccgtcacaa agagcttcaa caggggagag    720
tgttaa                                                                726

<210> SEQ ID NO 25
<211> LENGTH: 230
<212> TYPE: PRT
<213> ORGANISM: Artificial Sequence
<220> FEATURE:
<223> OTHER INFORMATION: Synthesized

<400> SEQUENCE: 25

Ile Ala Leu Ser Leu Ala Leu Val Thr Asn Ser Asp Ile Val Met Thr
1               5                   10                  15

Gln Ser Pro Leu Ser Leu Pro Val Thr Pro Gly Glu Pro Ala Ser Ile
            20                  25                  30

Ser Cys Arg Ser Ser Lys Ser Leu Leu Tyr Lys Asp Gly Lys Thr Tyr
        35                  40                  45

Leu Asn Trp Tyr Leu Gln Lys Pro Gly Gln Ser Pro Gln Leu Leu Ile
 50                  55                  60

Tyr Leu Met Ser Thr Arg Ala Ser Gly Val Pro Asp Arg Phe Ser Gly
 65                  70                  75                  80

Ser Gly Ser Gly Thr Asp Phe Thr Leu Lys Ile Ser Arg Val Glu Ala
                 85                  90                  95

Glu Asp Val Gly Val Tyr Tyr Cys Gln Gln Leu Val Glu Asp Pro Phe
            100                 105                 110

Thr Phe Gly Gln Gly Thr Lys Leu Glu Ile Lys Arg Thr Val Ala Ala
        115                 120                 125

Pro Ser Val Phe Ile Phe Pro Pro Ser Asp Glu Gln Leu Lys Ser Gly
130                 135                 140

Thr Ala Ser Val Val Cys Leu Leu Asn Asn Phe Tyr Pro Arg Glu Ala
145                 150                 155                 160

Lys Val Gln Trp Lys Val Asp Asn Ala Leu Gln Ser Gly Asn Ser Gln
                165                 170                 175

Glu Ser Val Thr Glu Gln Asp Ser Lys Asp Ser Thr Tyr Ser Leu Ser
            180                 185                 190

Ser Thr Leu Thr Leu Ser Lys Ala Asp Tyr Glu Lys His Lys Val Tyr
        195                 200                 205

Ala Cys Glu Val Thr His Gln Gly Leu Ser Ser Pro Val Thr Lys Ser
210                 215                 220

Phe Asn Arg Gly Glu Cys
225                 230

<210> SEQ ID NO 26
<211> LENGTH: 345
<212> TYPE: DNA
<213> ORGANISM: Artificial Sequence
<220> FEATURE:
<223> OTHER INFORMATION: Synthesized

<400> SEQUENCE: 26
gacatcgtga tgacccagtc ccctctgtcc ctgcctgtga cacccggaga gcctgcctcc      60
atcagctgca ggagctccaa gagcctgctg tacaaagacg gcaagaccta cctgaactgg     120
tatttacaga agcctggcca gtccccccag ctgctgatct acctcatgtc caccagggcc     180
tccggagtgc ctgatcggtt cagcggatcc ggcagcggca ccgatttcac cctcaagatc     240
tccagggtgg aggccgagga cgtgggagtg tactattgcc agcagctggt ggaggacccc     300
ttcaccttcg gccaaggcac aaagctggag atcaagagga ctgtg                     345

<210> SEQ ID NO 27
<211> LENGTH: 48
<212> TYPE: DNA
<213> ORGANISM: Artificial Sequence
<220> FEATURE:
<223> OTHER INFORMATION: Synthesized

<400> SEQUENCE: 27
aggagctcca agagcctgct gtacaaagac ggcaagacct acctgaac                   48

<210> SEQ ID NO 28
<211> LENGTH: 21
<212> TYPE: DNA
<213> ORGANISM: Artificial Sequence
<220> FEATURE:
<223> OTHER INFORMATION: Synthesized

<400> SEQUENCE: 28
ctcatgtcca ccagggcctc c    21

<210> SEQ ID NO 29
<211> LENGTH: 27
<212> TYPE: DNA
<213> ORGANISM: Artificial Sequence
<220> FEATURE:
<223> OTHER INFORMATION: Synthesized

<400> SEQUENCE: 29
cagcagctgg tggaggaccc cttcacc    27

<210> SEQ ID NO 30
<211> LENGTH: 69
<212> TYPE: DNA
<213> ORGANISM: Artificial Sequence
<220> FEATURE:
<223> OTHER INFORMATION: Synthesized

<400> SEQUENCE: 30
gacatcgtga tgacccagtc ccctctgtcc ctgcctgtga cacccggaga gcctgcctcc    60
atcagctgc    69

<210> SEQ ID NO 31
<211> LENGTH: 45
<212> TYPE: DNA
<213> ORGANISM: Artificial Sequence
<220> FEATURE:
<223> OTHER INFORMATION: Synthesized

<400> SEQUENCE: 31
tggtatttac agaagcctgg ccagtccccc cagctgctga tctac    45

<210> SEQ ID NO 32
<211> LENGTH: 96
<212> TYPE: DNA
<213> ORGANISM: Artificial Sequence
<220> FEATURE:
<223> OTHER INFORMATION: Synthesized

<400> SEQUENCE: 32
ggagtgcctg atcggttcag cggatccggc agcggcaccg atttcaccct caagatctcc    60
agggtggagg ccgaggacgt gggagtgtac tattgc    96

<210> SEQ ID NO 33
<211> LENGTH: 39
<212> TYPE: DNA
<213> ORGANISM: Artificial Sequence
<220> FEATURE:
<223> OTHER INFORMATION: Synthesized

<400> SEQUENCE: 33
ttcggccaag gcacaaagct ggagatcaag aggactgtg    39

<210> SEQ ID NO 34
<211> LENGTH: 115
<212> TYPE: PRT
<213> ORGANISM: Artificial Sequence
<220> FEATURE:
<223> OTHER INFORMATION: Synthesized

<400> SEQUENCE: 34

Asp Ile Val Met Thr Gln Ser Pro Leu Ser Leu Pro Val Thr Pro Gly

```
                1               5                   10                  15
            Glu Pro Ala Ser Ile Ser Cys Arg Ser Ser Lys Ser Leu Leu Tyr Lys
                            20                  25                  30

Asp Gly Lys Thr Tyr Leu Asn Trp Tyr Leu Gln Lys Pro Gly Gln Ser
                        35                  40                  45

Pro Gln Leu Leu Ile Tyr Leu Met Ser Thr Arg Ala Ser Gly Val Pro
                    50                  55                  60

Asp Arg Phe Ser Gly Ser Gly Ser Gly Thr Asp Phe Thr Leu Lys Ile
            65                  70                  75                  80

Ser Arg Val Glu Ala Glu Asp Val Gly Val Tyr Tyr Cys Gln Gln Leu
                            85                  90                  95

Val Glu Asp Pro Phe Thr Phe Gly Gln Gly Thr Lys Leu Glu Ile Lys
                        100                 105                 110

Arg Thr Val
                    115

<210> SEQ ID NO 35
            <211> LENGTH: 16
            <212> TYPE: PRT
            <213> ORGANISM: Artificial Sequence
            <220> FEATURE:
            <223> OTHER INFORMATION: Synthesized

<400> SEQUENCE: 35

Arg Ser Ser Lys Ser Leu Leu Tyr Lys Asp Gly Lys Thr Tyr Leu Asn
            1               5                   10                  15

<210> SEQ ID NO 36
            <211> LENGTH: 7
            <212> TYPE: PRT
            <213> ORGANISM: Artificial Sequence
            <220> FEATURE:
            <223> OTHER INFORMATION: Synthesized

<400> SEQUENCE: 36

Leu Met Ser Thr Arg Ala Ser
            1               5

<210> SEQ ID NO 37
            <211> LENGTH: 9
            <212> TYPE: PRT
            <213> ORGANISM: Artificial Sequence
            <220> FEATURE:
            <223> OTHER INFORMATION: Synthesized

<400> SEQUENCE: 37

Gln Gln Leu Val Glu Asp Pro Phe Thr
            1               5

<210> SEQ ID NO 38
            <211> LENGTH: 23
            <212> TYPE: PRT
            <213> ORGANISM: Artificial Sequence
            <220> FEATURE:
            <223> OTHER INFORMATION: Synthesized

<400> SEQUENCE: 38

Asp Ile Val Met Thr Gln Ser Pro Leu Ser Leu Pro Val Thr Pro Gly
            1               5                   10                  15

Glu Pro Ala Ser Ile Ser Cys
                        20
```

```
<210> SEQ ID NO 39
<211> LENGTH: 15
<212> TYPE: PRT
<213> ORGANISM: Artificial Sequence
<220> FEATURE:
<223> OTHER INFORMATION: Synthesized

<400> SEQUENCE: 39

Trp Tyr Leu Gln Lys Pro Gly Gln Ser Pro Gln Leu Leu Ile Tyr
1               5                   10                  15

<210> SEQ ID NO 40
<211> LENGTH: 32
<212> TYPE: PRT
<213> ORGANISM: Artificial Sequence
<220> FEATURE:
<223> OTHER INFORMATION: Synthesized

<400> SEQUENCE: 40

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 41
<211> LENGTH: 13
<212> TYPE: PRT
<213> ORGANISM: Artificial Sequence
<220> FEATURE:
<223> OTHER INFORMATION: Synthesized

<400> SEQUENCE: 41

Phe Gly Gln Gly Thr Lys Leu Glu Ile Lys Arg Thr Val
1               5                   10

<210> SEQ ID NO 42
<211> LENGTH: 97
<212> TYPE: PRT
<213> ORGANISM: Artificial Sequence
<220> FEATURE:
<223> OTHER INFORMATION: Synthesized

<400> SEQUENCE: 42

Gly Gly Gly Gly Thr Ala Cys Cys Cys Cys Gly Cys Cys Ala Cys
1               5                   10                  15

Cys Ala Thr Gly Gly Ala Gly Ala Cys Ala Gly Ala Cys Ala Cys Ala
            20                  25                  30

Cys Thr Cys Cys Thr Gly Cys Thr Ala Thr Gly Gly Gly Thr Ala Cys
            35                  40                  45

Thr Gly Cys Thr Gly Cys Thr Cys Thr Gly Gly Thr Thr Cys Cys
        50                  55                  60

Ala Gly Gly Thr Thr Cys Cys Ala Cys Thr Gly Gly Thr Gly Ala Gly
65                  70                  75                  80

Gly Thr Gly Cys Ala Ala Cys Thr Gly Gly Thr Gly Ala Ala Ala
                85                  90                  95

Gly

<210> SEQ ID NO 43
<211> LENGTH: 29
<212> TYPE: PRT
<213> ORGANISM: Artificial Sequence
<220> FEATURE:
<223> OTHER INFORMATION: Synthesized
```

```
<400> SEQUENCE: 43

Gly Gly Cys Thr Cys Thr Ala Gly Ala Thr Cys Ala Thr Thr Thr Thr
1               5                   10                  15

Cys Cys Gly Ala Gly Gly Gly Ala Cys Ala Gly Gly Gly
                20                  25

<210> SEQ ID NO 44
<211> LENGTH: 97
<212> TYPE: DNA
<213> ORGANISM: Artificial Sequence
<220> FEATURE:
<223> OTHER INFORMATION: Synthesized

<400> SEQUENCE: 44
ggggtaccgc cgccaccatg gagacagaca cactcctgct atgggtactg ctgctctggg       60
ttccaggttc cactggtgac atcgtgatga cccagtc                                97

<210> SEQ ID NO 45
<211> LENGTH: 32
<212> TYPE: DNA
<213> ORGANISM: Artificial Sequence
<220> FEATURE:
<223> OTHER INFORMATION: Synthesized

<400> SEQUENCE: 45
ggctctagat taacactctc ccctgttgaa gc                                     32
```

ANTI-HUMAN PD-1 HUMANIZED MONOCLONAL ANTIBODY AND APPLICATION THEREOF

APPLICATIONS

This application claims priority for the Chinese patent application "Anti-Human PD-1 Humanized Monoclonal Antibody and Its Applications", with filing date May 24, 2016 and application number 201610345750.1. All the contents of present invention are combined in this application by reference.

REFERENCE TO SEQUENCE LISTING SUBMITTED ELECTRONICALLY

The official copy of the sequence listing is submitted electronically via EFS-Web as an ASCII formatted sequence listing with a file named "KGI1-PAU06NS-Seq_List.txt", created on Sep. 11, 2018, and having a size of 32 kilobytes and is filed concurrently with the specification. The sequence listing contained in this ASCII formatted document is part of the specification and is herein incorporated by reference in its entirety.

FIELD OF THE INVENTION

The present invention relates to the biomedicine field, in particular to an anti-human PD-1 humanized monoclonal antibody and its applications.

BACKGROUND OF THE INVENTION

T-cell activation requires two signals. Signal 1 is antigen-specific and combined by T-cell antigen receptor (TCR) and antigen peptide-MHC complex; and signal 2 is a non-antigen-specific co-stimulating signal, which is combined by the receptor of adhesion molecule on T-cell and corresponding ligand on antigen presenting cell (APC). Signal 2 plays an important role in the activation of T-cell. Without signal 2 provided by co-stimulating molecules, T-cells will fall in a non-responsive state or apoptosis after recognizing antigens. The binding of CD28/CTLA-4 and its ligands B7-1 and B7-2 provides necessary co-stimulatory pathway for T-cell activation, which participates in the antigen-specific humoral and cellular immunity of organism. New members of CD28-B7 family include: ICOS (inducible costimulator) and its ligand B7RP-1, as well as PD-1 (programmed death-1) and its ligands PD-L 1 and PD-L2. CD28 and ICOS transmit co-stimulatory (positive) signals, whereas CTLA-4 and PD-1 transmit inhibitory (negative) signals. The balance between positive and negative signals of T-cell activation is critical in preventing foreign antigen invasion and autoimmune response.

PD-1, a transmembrane protein of 55KD, is a member of the immunoglobulin superfamily. This superfamily also includes CD28, ICOS and CTL (cytotoxicity T lymphocyte)-related antigen 4 (CTLA-4). Only one IgV sample region exists in the extracellular region, which is 23% homologous to CTLA-4, but does not have the MYPPPY motif which is necessary to bind B7-1/B7-2. There are two tyrosine residues in the cytoplasmic region and one ITIM (immunoreceptor tryosine-based inhibitory motif) in the tail, without YXXM motif. Other members of CD28 family exist in the form of homodimers linked by disulfide bonds, while PD-1 exists as monomers. Unlike the limited expression of CD28 and CTLA-4 (mainly in T-cells), PD-1 can be expressed in activated T-cells, B-cells and bone marrow cells, as well as CD4-CD8-thymic cells.

PD-1 has two ligands, PD-L1 (B7-H1) and PD-L2 (B7-DC), both of which are new members of B7 family and have a IgV sample region and a IgC sample region in extracellular region. PD-L1 contains 290 amino acids, whose extracellular domain is 20% and 15% homologous to B7-1 and B7-2, respectively. Its cytoplasmic region varies widely, but its secondary structure is very similar to B7-1 and B7-2. At gene level, PD-L2 is 37.4% homologous to PD-L1. In terms of expression and regulation, PD-L1 is different from PD-L2. PD-L1mRNA is rich in non-lymphoid tissues such as placenta, heart, lung and skeletal muscle, but PD-L1 protein can hardly be detected in normal tissues except macrophage-like cells and placental trophoblast. PD-L1 can be expressed on APC, T-cells and endothelial cells via induction, and it is rich in many kinds of human tumors. On the contrary, PD-L2 is only expressed on dendritic cells (DC) and monocytes. After treating DCs and monocytes with IFN-γ, the expressions of PD-L1 and PD-L2 are both up-regulated. However, PD-L1 and PD-L2 are actually regulated by Th1 and Th2 cells, respectively. On macrophages, IFN-γ secreted by Th1 cells can up-regulate the expression of PD-L1 through transcription factor STAT1, while IFN-γ requires IL-4 to induce PD-L2 expression. STATE is involved in signal transduction downstream of IL-4, suggesting that PD-L2 expression is regulated by Th2 cells.

PD-1 is an immunosuppressive receptor that interacts with its ligands PD-L1 and PD-L2 to transmit inhibitory signals and provides negative regulation in immune response. The combination of PD-1 and PD-L1/PD-L 2 inhibits the proliferation of lymphocytes and the production of cytokines (IL-2, IFN-γ and IL-10) mediated by TCR, resulting in cell cycle arrest, but without increasing cell death. Blocking the expressions of PD-L1 and PD-L2 on DC can improve the proliferation of T-cells and the production of cytokines (IFN-γ and IL-10), respectively. The effects will be stacked with each other when blocking the both, indicating that the functions of PD-L1 and PD-L2 are to inhibit the activation of T-cells. PD-1 can also participate in the negative regulation of B-cell response. PD-1 signal transduction inhibits B-cell proliferation, differentiation and Ig-type conversion, and plays an important role in establishing and/or maintaining peripheral self-tolerance. The molecular mechanisms of PD-1 inhibiting BCR-mediated signal transduction are: PD-1 dephosphorylates the important signal transducers of BCR signal transduction through its tyrosine phosphatase 2 in SH2 region (SHP-2), thereby inhibiting the tyrosine phosphorylation of effector molecules, including Ig β, Syk, PLC-γ2 and ERK1/2. The inhibition requires other tyrosine residues at ITIM C-terminal, instead of the tyrosine at the N-terminal.

PD-1 inhibits the activation of T-cells mediated by TCR, and weakens the effects of ICOS, IL-4 and IL-21, without hindering the effects of CD28, IL-7 and IL-15. However, the PD-1 signal transduction can inhibit the suboptimal co-stimulatory effect mediated by CD28. In some cases, PD-1-PD-L pathway may be secondary or reserved. Only when the CD28-B7 co-stimulatory pathway is absent or at a suboptimal level, can the pathway play a role in regulating the T-cell response. In other cases, this pathway plays a central role in T-cell activation or differentiation, which may depend on specific stages of the ongoing immune response. The relative level of inhibitory PD-L1/PD-L 2 and co-stimulatory B7-1/B7-2 signals on APC may affect the degree of T-cell activation and determine whether tolerance or autoimmunity is produced. The expression of PD-L1 in non-lymphoid tissues suggests that PD-1-PD-L may induce immune tolerance and regulate local inflammatory response by inhibiting autoreactive T-cells, B-cells and effector T-cells.

The ability of tumor cells to escape from the immune system is achieved by binding the programmed death ligand (PD-L1) generated on their surface with the PD-1 protein of T-cells. Tumor microenvironment in organism can induce infiltrating T-cells to overexpress PD-1 molecules. Tumor cells can overexpress PD-1's ligands, PD-L1 and PD-L2, resulting in persistent activation of PD-1 pathway in tumor microenvironment. The function of T-cells is inhibited so that it cannot discover tumors, nor issuing the immune system with treatment signal to attack and kill tumor cells.

PD-1 antibody is an antibody protein against PD-1, which prevents the first two proteins from binding, blocks the pathway, and partially restores the function of T-cells, allowing these cells to continue killing tumor cells. In July 2014, PMDA approved the full-humanized IgG4 anti-PD-1 monoclonal antibody Nivolumab to be launched in Japan for the treatment of advanced melanoma, which became the first PD-1 antibody approved by a major regulatory agency. In 2015, FDA approved two kinds of PD-1 antibodies, namely Keytruda (pembrolizumab) from Merck, and OPDIVO (nivolumab) from Bristol-Myers Squibb.

SUMMARY OF THE INVENTION

To solve these technical problems, the present invention aims to provide an anti-human PD-1 humanized monoclonal antibody with good specificity, high affinity and stability.

The first aspect of the invention relates to an anti-human PD-1 humanized monoclonal antibody or an antigen binding part thereof, which comprises a CDR region selected from a group of the following:

The sequences of heavy chains CDR1, CDR2 and CDR3 are shown as SEQ ID NO: 17-19, respectively. The sequences of light chains CDR1, CDR2 and CDR3 are shown as SEQ ID NO: 35-37, respectively, or includes sequences that bind antigenic epitopes same to above sequences.

Further, the anti-human PD-1 humanized monoclonal antibody or its antigen binding part in the invention, also includes sequences selected from the following framework regions of heavy chain variable region: FR1, FR2, FR3 and FR4, as shown in SEQ ID NO: 20-23, respectively, or other sequences that having greater than 70%, 80%, 85%, 90%, 95%, 99% identity to them, respectively.

Further, the anti-human PD-1 humanized monoclonal antibody or its antigen binding part in the invention, also includes sequences selected from the following framework regions of light chain variable region: FR1, FR2, FR3 and FR4, as shown in SEQ ID NO: 38-41, respectively, or other sequences that having greater than 70%, 80%, 85%, 90%, 95%, 99% identity to them, respectively.

Further, the anti-human PD-1 humanized monoclonal antibody or its antigen binding part in the invention, includes sequences selected from the following heavy chain variable region, as shown in SEQ ID NO: 16, or includes sequences that bind antigenic epitopes same to above sequences.

Further, the anti-human PD-1 humanized monoclonal antibody or its antigen binding part in the invention, also includes sequences selected from the following light chain variable regions, as shown in SEQ ID NO: 34, or other sequences that having greater than 70%, 80%, 85%, 90%, 95%, 99% identity to above sequences, respectively.

Specifically, for the anti-human PD-1 humanized monoclonal antibody or its antigen binding part in the invention, the sequence of heavy chain is as shown in SEQ ID NO: 8.

Specifically, for the anti-human PD-1 humanized monoclonal antibody or its antigen binding part in the invention, the sequence of light chain is as shown in SEQ ID NO: 25.

A nucleic acid molecule according to the second aspect of the invention contains a nucleic acid sequence that is capable of encoding an antibody heavy chain variable region, which comprises an amino acid sequence selected from the following group:

(1) SEQ ID NO: 17-19;
(2) Sequence that satisfies at least one of the following two requirements when compared with the sequence: a) binding to the same antigenic epitope; b) identity greater than 70%, 80%, 85%, 90% or 97%.

Further, the heavy chain variable region contains an amino acid sequence selected from the following group:

SEQ ID NO: 16, or the sequence that satisfies at least one of the following three requirements when compared with the sequence (1): a) binding to the same antigenic epitope; b) identity greater than 70%, 80%, 85%, 90% or 97%; c) containing substitution for one or more nucleotides in the framework region of the above mentioned sequence.

In the embodiments of the invention, the nucleic acid molecules contain selected sequences as shown in SEQ ID NO: 5.

Further, the nucleic acid molecule contains selected sequences as shown in SEQ ID NO: 7.

A nucleic acid molecule according to the third aspect of the invention contains a nucleic acid sequence that is capable of encoding an antibody light chain variable region, which comprises an amino acid sequence selected from the following group:

(1) SEQ ID NO: 35-37;
(2) Sequence that satisfies at least one of the following two requirements when compared with the sequence: a) binding to the same antigenic epitope; b) identity greater than 70%, 80%, 85%, 90% or 97%.

Further, the light chain variable region contains an amino acid sequence selected from the following group:

SEQ ID NO: 34, or the sequence that satisfies at least one of the following three requirements when compared with the sequence: a) binding to the same epitope; b) identity greater than 70%, 80%, 85%, 90% or 97%; c) containing substitution for one or more nucleotides in the framework region of the above mentioned sequence.

In the embodiments of the invention, the nucleic acid molecules contain selected sequences as shown in SEQ ID NO: 26.

Further, the nucleic acid molecule contains selected sequences as shown in SEQ ID NO: 24.

The fourth aspect of the invention relates to a carrier which contains nucleic acid molecules as described in the second or third aspect of the invention.

Further, the carrier referred to in the invention contains any nucleic acid molecule as described in the second and third aspects of the invention.

The fifth aspect of the invention relates to host cells, which contain any nucleic acid molecule as described in the second or third aspect of the invention, or any carrier as described in the fourth aspect of the invention.

The sixth aspect of the invention relates to conjugates, which contain any anti-human PD-1 humanized monoclonal antibody or its antigen binding part as described in the first aspect of the invention, and other bioactive substances. The anti-human PD-1 humanized monoclonal antibody or its antigen binding part is directly or through junction fragments, coupled with other bioactive substances.

In the embodiment of the invention, the other bioactive substances are selected from chemicals, toxins, peptides, enzymes, isotopes, or cytokines that can directly or indirectly inhibit cell growth or kill cells, or inhibit or kill cells by activating the immune response of organism for the treatment of tumors, or selected from other single or mixed substances with biological activity.

The seventh aspect of the invention relates to compositions (e.g. pharmaceutical composition), which contain any anti-human PD-1 humanized monoclonal antibody or its antigen binding part as described in the first aspect of the invention, any nucleic acid molecule as described in the second or third aspect, any carrier as described in the fourth aspect, any host cell as described in the fifth aspect, or any conjugate as described in the sixth aspect, as well as optional pharmaceutically acceptable carriers or excipients, and optional other bioactive substances.

In accordance with any composition (e.g. pharmaceutical composition) as described in the seventh aspect of the invention, the other bioactive substances include, but are not limited to, other antibodies, fusion proteins or drugs (e.g. anti-tumor drugs, such as radiotherapy and chemotherapy drugs).

The invention also relates to diagnostic reagents or kits, which contain any anti-human PD-1 humanized monoclonal antibody or its antigen-binding part as described in the first aspect of the invention. The diagnostic reagents or kits are used in vitro (e.g. cells or tissues) or in vivo (e.g. human or animal models) to diagnose diseases associated with PD-1 (e.g. tumors or virus infection, such as virus infection or tumor with overexpression of PD-L1).

In the embodiment of the present invention, the tumors include, but are not limited to, lung cancer, ovarian cancer, colon cancer, rectal cancer, melanoma, renal cancer, bladder cancer, breast cancer, liver cancer, lymphoma, malignant hematopathy, head & neck cancer, glioma, gastric cancer, nasopharyngeal cancer, laryngeal cancer, cervical cancer, uterine body cancer, osteosarcoma, thyroid cancer, and prostatic cancer. The virus infections include, but are not limited to, acute, subacute or chronic HBV, HCV and HIV infections.

The invention also relates to any anti-human PD-1 humanized monoclonal antibody or its antigen binding part as described in the first aspect of the invention, any nucleic acid molecule as described in the second or third aspect, any carrier as described in the fourth aspect, any host cell as described in the fifth aspect, any conjugate as described in the sixth aspect, or any composition as described in the seventh aspect which is used to prepare medicines for the prevention or treatment of PD-1 associated diseases (e.g. tumors, microbial or virus infection, such as tumor or virus infection overexpression of PD-L1).

In the embodiment of the present invention, the tumors include, but are not limited to, lung cancer, ovarian cancer, colon cancer, rectal cancer, melanoma, renal cancer, bladder cancer, breast cancer, liver cancer, lymphoma, malignant hematopathy, head & neck cancer, glioma, gastric cancer, nasopharyngeal cancer, laryngeal cancer, cervical cancer, uterine body cancer, osteosarcoma, thyroid cancer, and prostatic cancer. The microbial infections include, but are not limited to, bacterial, fungal and protozoal infections. The virus infections include, but are not limited to, acute, subacute or chronic HBV, HCV and HIV infections.

The following is a further description of the invention, where unless otherwise specified, the scientific and technical terms used herein have meanings commonly understood by those skilled in the art. In addition, the terms used in this document, including those related to protein and nucleic acid chemistry, molecular biology, cell and tissue culture, microbiology, immunology and laboratory procedures, refer to terms or procedures widely used in their fields. The following terms are defined and explained here to ensure a better understanding of the present invention.

In the present invention, the term "antibody" refers to an immunoglobulin molecule normally consisted of two pairs of identical polypeptide chains, each with a "light" (L) chain and a "heavy" (H) chain. The light chains of antibody can be classified as κ and λ light chains. The heavy chains can be classified as μ, δ, γ, α and ε, with antibody isotypes defined as IgM, IgD, IgG, IgA and IgE, respectively. In light and heavy chains, the variable region and the constant region are linked with each other through the "J" region of about 12 or more amino acids, and the heavy chain also contains the "D" region of about three or more amino acids. Each heavy chain is consisted of a heavy chain variable region ($V_H$) and a heavy chain constant region (CH). The heavy chain constant region is consisted of 3 domains ($C_H1$, $C_H2$ and $C_H3$). Each light chain is consisted of a light chain variable region ($V_L$) and a light chain constant region ($C_L$). The light chain constant region is consisted of a domain CL. The constant region of antibody can mediate the binding of immunoglobulins to host tissues or factors, including various cells of the immune system (e.g. effector cells) and the first component of classical complement system (C1q). The $V_H$ and $V_L$ regions can also be subdivided into highly variable regions (called as complementary determinant regions (CDR)), amongst of which conservative regions known as framework regions (FR) are distributed. Each VH or VL region is consisted of three CDRs and four FRs arranged from the amino terminal to the carboxyl terminal in the following order: FR1, CDR1, FR2, CDR2, FR3, CDR3, FR4. The variable regions ($V_H$ and $V_L$) of each heavy/light chain pair form antibody binding sites separately. The distribution of amino acids to regions or domains follows the definitions in Kabat Sequences of Proteins of Immunological Interest (National Institutes of Health, Bethesda, Md. (1987and 1991)), or in Chothia & Lesk (1987) J.Mol-.Biol.196:901-917; Chothia et al. (1989) Nature 342: 878-883. The term "antibody" is not limited by any specific antibody production method. For example, it particularly includes recombinant antibodies, monoclonal antibodies and polyclonal antibodies. Antibodies can be of different types, such as IgG (e.g. IgG1, IgG2, IgG3 or IgG4 subtypes), IgA1, IgA2, IgD, IgE, or IgM antibody.

In the present invention, the term "antigen-binding part" of an antibody refers to one or more parts of a full-length antibody that retain the ability of binding the same antigen (e.g. PD-1) of the antibody, so as to compete with the intact antibody for antigen specific binding. Usually, see Fundamental Immunology, Ch.7 (Paul, W., ed., 2nd Edition, Raven Press, N.Y. (1989)), which is incorporated in this article by citation for all purposes. The antigen binding part can be produced by recombinant DNA technology or by enzymatic or chemical cleavage of intact antibody. In some cases, the antigen binding part includes Fab, Fab', F (ab') 2, Fd, Fv, dAb, and complementary determinant region (CDR) fragments, single chain antibodies (e.g. scFv), chimeric antibodies, diabodies and such kind of peptides, which contain at least a part of the antibody sufficient to give the peptides a capacity for antigen specific binding.

With the above scheme, the present invention has at least the following advantages: the invention obtains an anti-human PD-1 humanized monoclonal antibody with good specificity, high affinity and stability by screening, and the antibody can specifically bind to human PD-1 instead of binding to other members of CD28 family, so it can significantly inhibit the growth of tumor.

The above description is only an overview of the technical scheme of the present invention. In order to have a better understanding of the technical means of the invention and to implement in accordance with the specifications, see following details based on good embodiments of the invention and the description of the figures.

EMBODIMENTS

Figure 1:
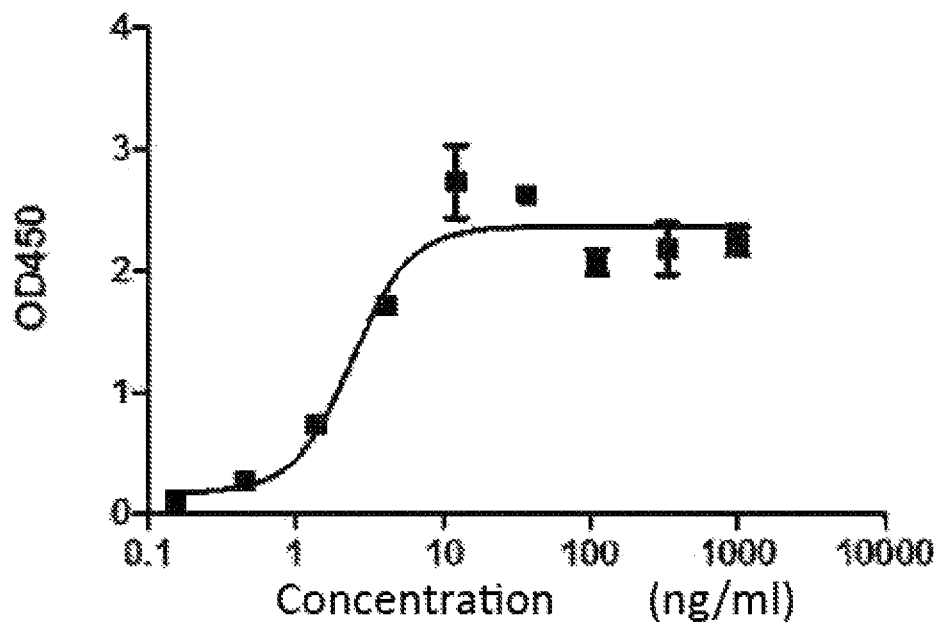
FIG. 1 shows the result of ELISA binding activity of mouse PD-1 antibody.

The invention is described in detail as follows through Figures and embodiments. The following embodiments are used to illustrate the present invention, but not to limit the scope of the invention.

Embodiment 1: Screening of Mouse Antibody 1.1 Animal Immunity

The classical immunization schedule is used to immunize BALB/c mice. The immunogen is hPD-1 (human PD-1) protein (purchased from Beijing Yiqiao Shenzhou Biotechnology Co., Ltd.) so that the mice can produce anti-hPD-1 antibodies. The specific scheme is shown in Table 1:

TABLE 1

Animal Immunization Scheme for hPD-1 Protein

| Step | Days | Method |
|---|---|---|
| Preimmune serum collection | −4 | Collect blood at orbital cavity, expect to obtain serum of 15-30 μL and store at −20° C. |
| Primary immunization | 0 | Cell immunogen: PD1 overexpressed cell |
| First boosted immunization | 14 | Cell immunogen: PD1 overexpressed cell |
| Second boosted immunization | 35 | Same to booster immunization 1. Cell immunogen: PD1 overexpressed cell |
| Valence measurement by serum collection | 42 | Collect blood at orbital cavity to obtain serum of 15-30 μL. |
| Final immunization | 56 | Amount of immunogen (FD1-FC): 50 μg; injection method: IV (intravenous injection) |
| Feeding cells preparation | 58 | Six mice needed for each time (aged about 10 weeks) 1. Remove eyeballs from unimmunized mice to collect blood. Separate the serum to use it as the negative control serum in antibody detection. Kill the mice by cervical dislocation, soak them in 75% ethyl alcohol for 5 min, and then fix them on dissecting table. 2. Use sterilizing tweezer to raise abdominal skin from posterior abdomen, so as to expose the peritoneum. Disinfect the peritoneum with alcohol wipes. 3. Inject 10 mL medium by syringe into the abdominal cavity, without passing through the intestinal canal. Fix the syringe with right hand to keep the needle staying in the abdominal cavity. Hold the alcohol wipe with left hand to flip the abdomen for 1 min, and then suck out the injected culture fluid. |
| Spleen harvest | 59 | Kill the mice to collect spleens. Put the spleens into a 10 mL plate with no serum medium. Use a needle to break the spleens and use a plunger to slightly press them, so as to collect immune spleen cells. Filter with a 200-mesh screen, centrifuge at 1200 rpm for 5 min, and remove supernatant. Use RBC lysate buffer to re-suspend the spleen cells, centrifuge at 1200 rpm for 5 min, then wash with serum-free medium for one time, and re-suspend by 20 mL serum-free medium. Count the cells and store them under 4° C. |

1.2 Cell Fusion and Screening of Hybridoma Cell

Before fusion, the state of mouse myeloma SP2/0 is adjusted to ensure that its growth density does not exceed $1.0\times10^6$ cells. The final immunization is carried out 3 days ahead of schedule, for which tail vein injection is used. The feeding cells are prepared 1 day ahead of schedule, with plate layout of $2.0\times10^4$ cells/well. By PEG fusion, the ratio of spleen cells to SP2/0 cells is between 10:1 and 5:1, and the number of spleen cells per well is up to $1.0\times10^5$. After 7 days of fusion, harvest the supernatant and replace the medium.

The harvested supernatant is first screened by direct ELISA binding method. After expansion on obtained positive clones, re-screen the supernatant.

Two rounds of re-screening are carried out through cell binding and inhibition experiments. The positive clones obtained by screening are subcloned by limited dilution method and arranged on 96-well plates, which are 5 clones/well, 2 clones/well and 1 clone/well. After 7 days of culture, the positive subclones are selected by direct ELISA binding experiment, and then expanded and preserved.

The specific steps involved in each experiment method are as follows:

A. ELISA binding method

Envelop HPD-1-Fc on the plate, add gradient diluted antibody, incubate and wash it, and then add goat anti-mouse-HRP, perform coloration, and draw up the reaction curve by fitting of readings to calculate the EC50 value.

B. Cell binding experiment

Lay the over-expressed hPD-1-Fc cells on the cell plate for culture inspection one day ahead of schedule. After closure on the next day, add gradient-diluted antibody, then anti-mouse-EU, and obtain the readings.

C. Cell inhibition experiment

Lay the over-expressed hPD-1-Fc cells on the cell plate for culture inspection one day ahead of schedule. After closure on the next day, add gradient-diluted antibody, then PD1-Fc-Biotin, then Europium-labeled streptavidin, and obtain the readings.

1.3 Preparation and Activity Identification of Mouse Antibody

Inoculate the hybridoma cells of selected positive subclones into SFM medium for about 7 days. Collect the supernatant and purify it with Protein G purification column after centrifugal filtration. Then test the purified antibodies for ELISA binding activity, ELISA inhibitory activity, cell binding activity, cell inhibitory activity and MLR. After screening, obtain a mouse anti-PD-1 monoclonal antibody with the highest activity, and name it as mouse anti-PD-1.

The specific steps involved in each experiment method are as follows:

A. ELISA binding activity

Envelop PD1-His on the plate, add gradient diluted antibody, incubate and wash it, and then add goat anti-mouse-HRP, perform coloration, and draw up the reaction curve by fitting of readings (see FIG. 1 for results) to calculate the EC50 value. The binding activity EC50 to hPD-1 is 2.402 ng/mL.

B. ELISA inhibitory activity

Figure 2:
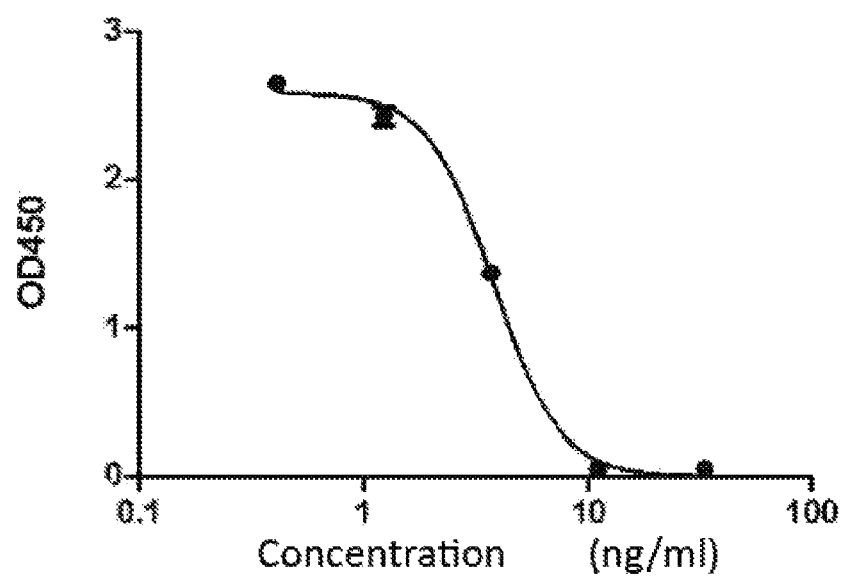
FIG. 2 shows the result of ELISA inhibitory activity of mouse PD-1 antibody.

Incubate the gradient diluted antibody and a certain concentration of PD1-Fc-His in advance, then add the mixture to the plate enveloped with PD1-Fc. Add anti-His-HRP to the plate after incubating and washing. Then perform coloration. Draw up the reaction curve by fitting of readings (see FIG. 2 for results) to calculate the IC50 value. The inhibitory activity IC50 is 3.827 nM.

C. Cell binding activity

Figure 3:
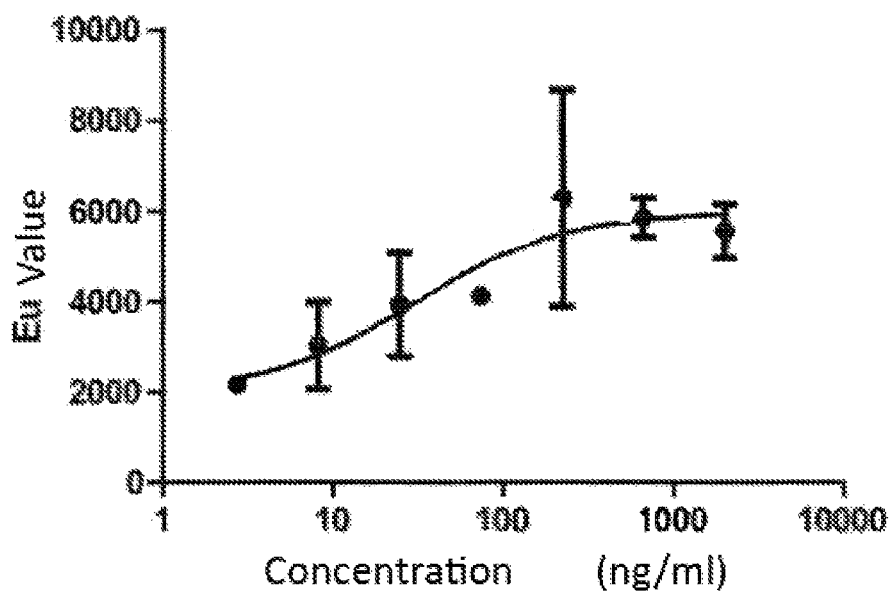
FIG. 3 shows the result of cell binding activity of mouse PD-1 antibody.

Lay PD1-27 (PD1 over-expressed CHO-K1 stable transfected cells) on the cell plate for culture inspection one day ahead of schedule. After closure on the next day, add gradient-diluted antibody, then anti-mouse-EU after washing, then fluorescence enhancement solution after washing, and obtain the readings. Draw up the reaction curve by fitting of readings (see FIG. 3 for results) to calculate the cell binding activity EC50 which is 87.80 ng/mL.

D. Cell inhibitory activity

Figure 4:
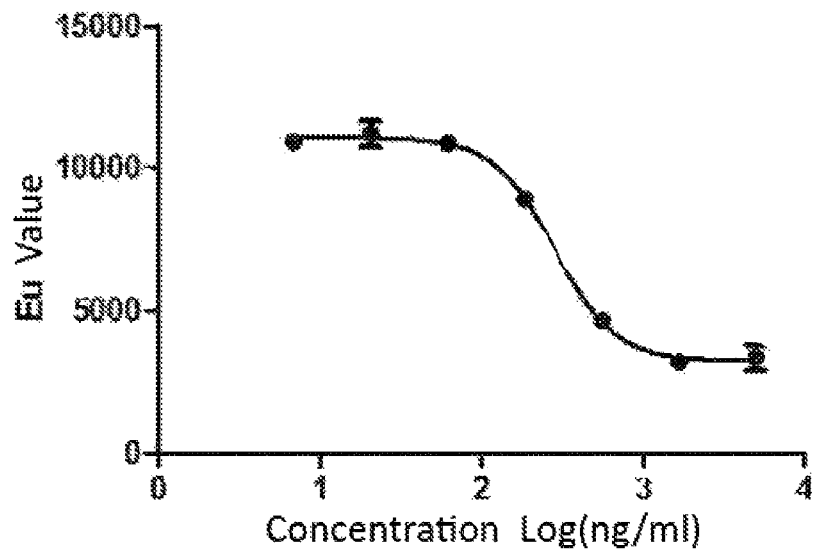
FIG. 4 shows the result of cell inhibitory activity of mouse PD-1 antibody.

Lay PD1-27 (PD1 over-expressed CHO-K1 stable transfected cells) on the cell plate for culture inspection one day ahead of schedule. After closure on the next day, add gradient-diluted antibody and PD1-Fc, then anti-Human-EU after washing, and then fluorescence enhancement solution after washing. Draw up the reaction curve by fitting of readings (see FIG. 4 for results) to calculate the cell inhibitory activity IC50 which is 284.1 ng/mL.

E. MLR experiment

Figure 5:
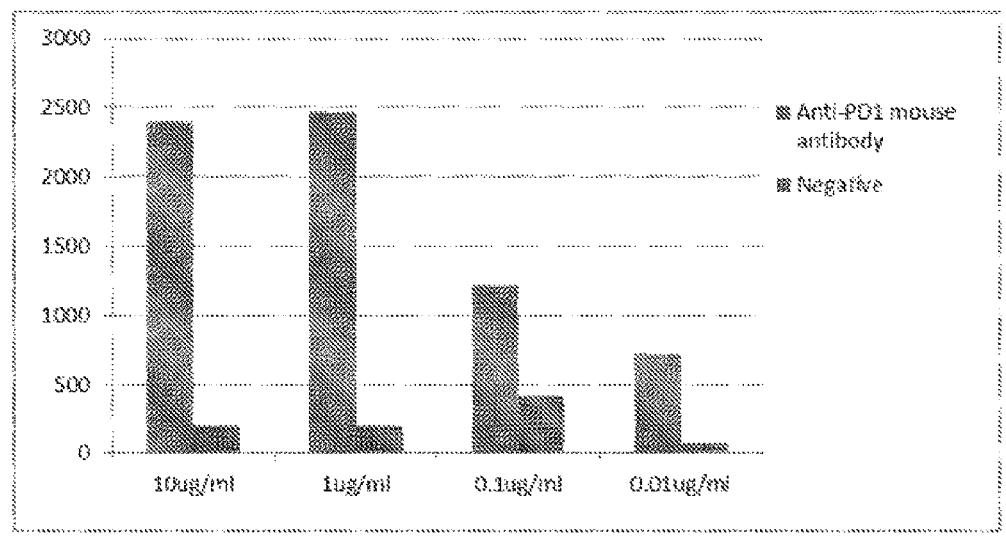
FIG. 5 shows the result of MLR experiment of mouse PD-1 antibody.

Mix in proportion CD4+ T cells and DC cells that are separated by magnetic beads and lay the mixture on the plate. Then add different concentrations of anti-PD1 mouse monoclonal antibody. After 5 days of culture, detect the concentration of IFN-γ by the kit. The results, as shown in FIG. 5, indicate that anti-PD1 mouse monoclonal antibody can significantly promote the expression of IFN-γ.

Embodiment 2: Humanization and Affinity Maturation of Mouse Antibody

2.1 Acquisition of Mouse Antibody Genes

Use Purelink RNA Micro kit to extract mouse anti-PD-1 hybridoma total RNA, then use PrimeScript™ II 1st Strand cDNA Synthesis Kit to make the reverse transcription of total RNA and prepare cDNA. Use Leader primer to expand the variable regions of heavy and light chains separately. The reaction system and PCR conditions are shown in Tables 2 and 3, respectively.

TABLE 2

PCR reaction system of mouse antibody gene cDNA

| Reagent name | Volume added |
| --- | --- |
| 10x Buffer | 5 μL |
| 10 μM dNTP Mix | 1 μL |
| 50 mM MgSO4 | 2 μL |
| Upstream and downstream primers | 1 μL for each |
| cDNA template | 1 μL |
| Taq | 0.2 μL |
| ddH2O | up to 50 μL |

TABLE 3

PCR reaction conditions of mouse antibody gene cDNA

| Temperature | Time | |
| --- | --- | --- |
| 94° C. | 5 min | |
| 94° C. | 30 s | Totally 30 cycles |
| 50° C. | 30 s | |
| 68° C. | 45 s | |
| 68° C. | 7 min | |

Cool to 4° C.

The PCR results are analyzed by electrophoresis. Add 0.5 μl LA Taq enzyme into the reaction tube containing expansion products and react 10 min at 72° C. After that, perform enzyme linking and the reaction system is as shown in Table 4.

TABLE 4

| Enzyme linked reaction system | |
| --- | --- |
| Reagent name | Volume added |
| PMD18-T | 1 μL |
| Reaction product | 4 μL |
| Solution I | 5 μL |
| Reaction at 16° C. for 1 h | |

After the enzyme linking, transform, select clones and conserve the breed, then obtain the anti-human PD-1 antibody. After sequencing, the nucleic acid sequence and amino acid sequence of heavy chain variable region are obtained and shown as SEQ ID NO: 1 and 2, respectively. The nucleic acid sequence and amino acid sequence of light chain variable region are obtained and shown as SEQ ID NO:3 and 4, respectively.

2.2 Humanization Design

By analyzing the sequence of mouse antibody and comparing with human germ line gene, it is confirmed that the heavy chain FR1 template comes from HM855688 (IGHV3-21*04); the heavy chain FR2 template comes from L06614 (IGHV3-30*07); the heavy chain FR3 template comes from M77327 (IGHV3-30*15); and the humanized template of light chain is X63397 (IGKV2-28*01). By CDR-grafting, the CDRs of heavy and light chains are juxtaposed into the framework sequence to construct humanized antibodies and synthesize fragments of humanized antibody variable regions. The nucleic acid sequences of heavy and light chain variable regions are obtained and shown as SEQ ID NO:5 and SEQ ID NO:6, respectively.

2.3 Construction of Antibody Library

The DNA sequence of mouse antibody CDR is analyzed to identify the mutation site in variable region CDR. The primer sequence is designed, and the location of the mutation site is designed as NNS to encode any amino acid. By using humanized antibody scFv as template, the scFv antibody library is expanded by PCR. The scFv antibody library is constructed into phage plasmid through sfiI digestion site, so as to build the secondary antibody library.

2.4 Screening of Antibody Library

Afterwards, the high affinity antibodies are screened by phage display, where the specific method is as follows:

A. Transform the phage plasmids of antibody library containing scFv into *Escherichia coli* TG1 by electroporation. After recovery at 37° C., 220 rpm for 1 h, add the helper phage to the remaining bacteria solution, and add ampicillin. Then cultivate at 37° C., 220 rpm for 1 h. Centrifuge at 2500 rpm×5 min to remove the supernatant, and sowing bacteria with 2×YT-AK medium, then cultivate it at 37° C. and 220 rpm overnight.

B. Envelop antigen: dilute PD1-Fc-His with enveloping buffer, mix it and add it into the immune tube and envelop overnight at 4° C.

C. Collection of recombinant phage: centrifuge the overnight culture medium at 2500 rpm×5 min, collect 10 ml supernatant, add 2 ml PEG/NaCl, mix and place it on ice for 30-60 min. Afterwards, centrifuge for 10000 g×20 min, then remove the supernatant and dissolve the phage library by 2×YT medium.

D. Blocking: wash the immune tube with PBS twice, add the blocking buffer and then place at room temperature for 1 h. In addition, mix the blocking solution with the same volume of phage library to block 10-15 min at room temperature.

E. Incubate phage library: wash the immune tube twice with PBS, add blocked phage library and then incubate it at 37° C. for 2-3 h.

F. Elution: add 100 ml TG1 bacteria solution (inoculated the day before) into 10 ml 2×YT and culture it to A600 value of 0.4-0.5 at 37° C., 220 rpm. Wash the immune tube with PBST for 8 times, then wash with PBS twice, add 5 ml bacteria solution with logarithmic growth phase and then cultivate at 37° C., 220 rpm for 1 h.

G. Output: dilute the bacteria solution to $10^{-1}$ and $10^{-2}$, and apply 100 ul on the plate.

H. Next round of screening: add 200 μl helper phage into 5 ml eluted bacteria solution, then add 5 μl ampicillin into the bacteria solution, and cultivate at 37° C., 220 rpm for 1 h. Centrifuge at 2500 rpm×5 min to remove the supernatant, and sow bacteria with 10 ml 2×YT-AK, then cultivate it at 37° C. and 220 rpm overnight.

Repeat Steps B-H.

After 3 rounds of screening, select monoclones and prepare recombinant phages. Phage ELISA method is used to detect the activity of recombinant phages. See below for details:

A. Envelop hPD-1-FC and cultivate overnight at 4° C.;

B. Wash with PBST for twice, add phage supernatant, and cultivate at 25° C. for 1 h;

C. Wash with PBST for three times, add diluted anti-M13-biotinAb, and place at 25° C. for 1 h;

D. Wash with PBST for three times, add diluted HRP-streptavidin, and place at 25° C. for 1 h;

E. Wash with PBST for three times, add preheated TMB and cultivate at 25° C. for 10 min. Add 1M H2SO4 to stop the reaction, and detect the absorbance by OD450. Select positive clones and send them for sequencing. The heavy or light chain variable region is spliced into the corresponding constant region sequence of human antibody by PCR. The full length fragments of expanded antibody heavy and light chains (including signal peptide) are cloned into pcDNA3.1GS. Light-chain and heavy-chain plasmids are co-transfected into EXPI 293 cell line. After 7 days of culture, the supernatant is purified by Protein A (GE), and finally antibodies with mature affinity are obtained. Antibodies with mature affinity separately undergo detections of Elisa binding activity, Elisa inhibitory activity and Cell binding activity.

A. ELISA Binding Activity

Figure 6:
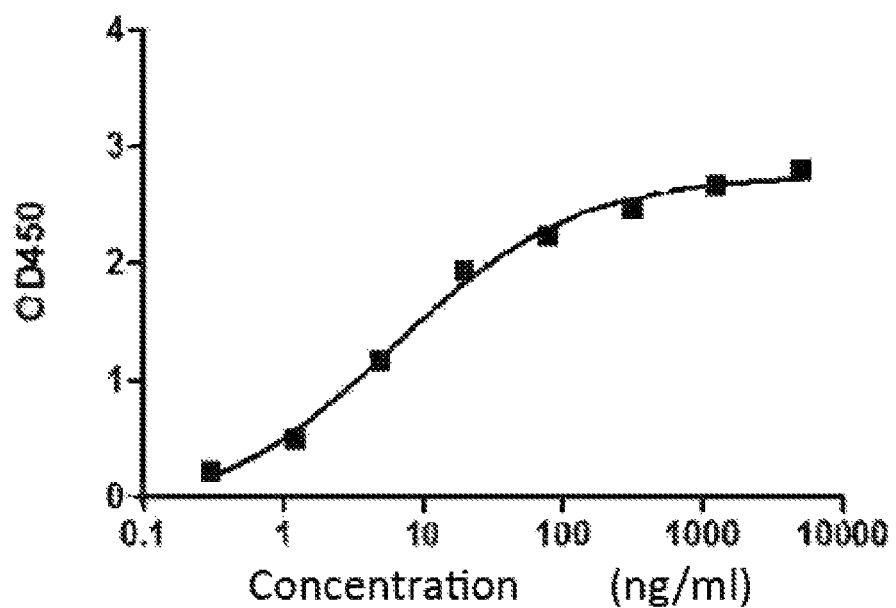
FIG. 6 shows the result of ELISA direct binding activity of humanized PD-1 antibody.

Lay PD1-His on the plate, add gradient diluted antibody, incubate and wash it, and then add goat anti-mouse-HRP, perform coloration, and draw up the reaction curve by fitting of readings (see FIG. 6 for results) to calculate the EC50 value. The binding activity EC50 to hPD-1 is 6.094 ng/mL.

B. ELISA Inhibitory Activity

Figure 7:
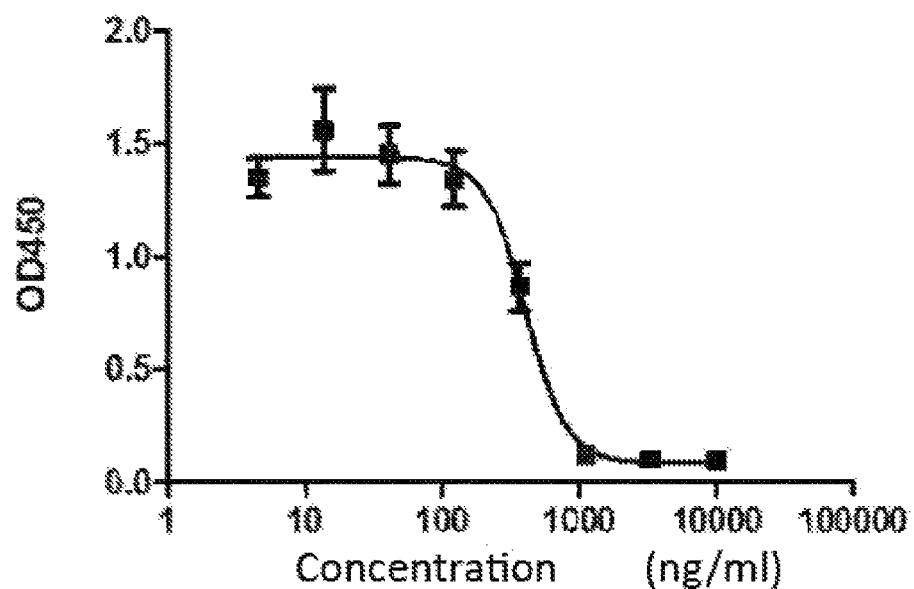
FIG. 7 shows the result of ELISA inhibitory binding activity of humanized PD-1 antibody.

Incubate the gradient diluted antibody and a certain concentration of PD1-Fc-His in advance, then add the mixture to the plate laid with PD1-Fc. Add anti-His-HRP to the plate after incubating and washing. Then perform coloration. Draw up the reaction curve by fitting of readings (see FIG. 7 for results) to calculate the IC50 value. The inhibitory activity IC50 is 406.1 nM.

C. Cell binding activity

Figure 8:
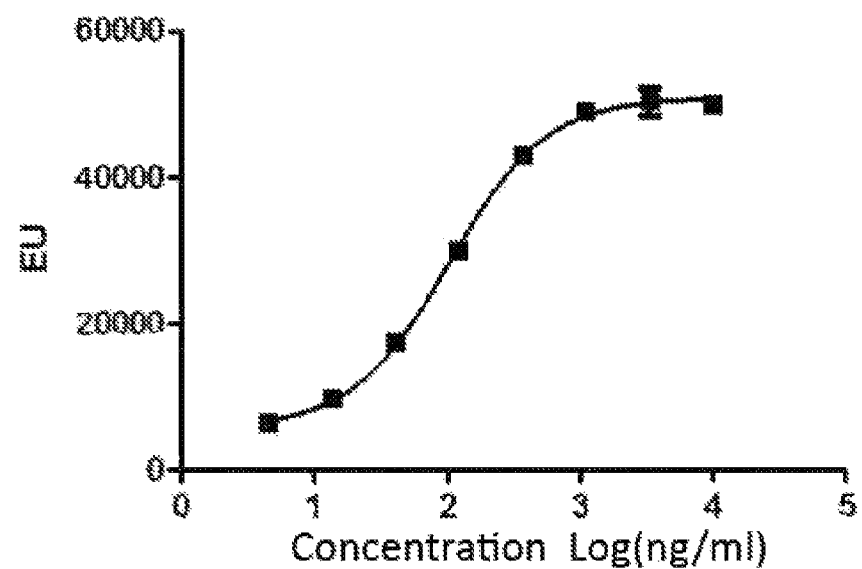
FIG. 8 shows the result of cell binding activity of humanized PD-1 antibody.

Lay PD1-27 (PD1 over-expressed CHO-K1 stable transfected cells) on the cell plate for culture inspection one day ahead of schedule. After closure on the next day, add gradient-diluted antibody, then anti-mouse-EU after washing, then fluorescence enhancement solution after washing, and obtain the readings. Draw up the reaction curve by fitting of readings (see FIG. 8 for results) to calculate the cell inhibitory activity IC50 which is 103.2 ng/mL.

2.5 Screening Result of Antibodies

After 3 rounds of screening, 76 monoclones are selected for testing and 40 of them are selected for sequencing. The results show that the cloned sequence is consistent with that of the original humanized antibody variable region. The sequence of humanized antibody variable region is spliced with that of human antibody constant region to form the whole antibody sequence. Construct expression plasmids P3.1GS-hup01-HC and P3.1GS-hup01-LC and the transient transfected 293 cell to prepare the antibody and check the antibody activity.

Anti-PD-1 heavy chain nucleotide sequence and amino acid sequence are shown in SEQ ID NO:7 and 8, respectively. Among them, the nucleotide sequence of heavy chain variable region is:

(SEQ ID NO: 5)
GAGGTGCAACTGGTGGAAAGCGGCGGAGGACTGGTGAAGCCCGGAG

GATCCCTGAGGCTGTCCTGTGCCGCCTCC<u>GGCTTCACCTTCAGCAGCTAC</u>

<u>ACC</u>ATGTCCTGGGTGAGGCAGGCTCCCGGAAAGGGCCTGGAGTGGGTGGC

TAC<u>ATCAGCAACGGAGGCTCCTTCACC</u>TATTACCCTGACTCCATGAAGG

GCAGGTTCACAATCTCCCGGGACAACTCCAAGAACACCCTGTACCTGCAG

ATGTCCAGCCTGAGGGCTGAGGACACCGCCGTGTATTACTGC<u>GCCAGGGA</u>

<u>CAGCGACTATTACGGCATCTTCGACTAC</u>TGGGGCCAGGGAACAACCGTGA

CAGTGAGCTCC

The underlined parts represent CDR1, CDR2 and CDR3, with serial numbers SEQ ID NO:9-11, respectively, and the parts with no underline are FR1, FR2, FR3 and FR4 with serial numbers SEQ ID NO:12-15, respectively.

Accordingly, the amino acid sequence of heavy chain variable region is:

(SEQ ID NO: 16)
EVQLVESGGGLVKPGGSLRLSCAAS<u>GFTFSSYT</u>MSWVRQAPGKGLEWV
AT<u>ISNGGSFT</u>YYPDSMKGRFTISRDNSKNTLYLQMSSLRAEDTAVYYC<u>AR
DSDYYGIFDY</u>WGQGTTVTVSS

The underlined parts represent CDR1, CDR2 and CDR3, with serial numbers SEQ ID NO:17-19, respectively, and the parts with no underline are FR1, FR2, FR3 and FR4 with serial numbers SEQ ID NO:20-23, respectively.

Anti-PD-1 light chain nucleotide sequence and amino acid sequence are shown in SEQ ID NO:24 and 25, respectively. Among them, the nucleotide sequence of light chain variable region is:

(SEQ ID NO: 26)
GACATCGTGATGACCCAGTCCCCTCTGTCCCTGCCTGTGACACCCGG

AGAGCCTGCCTCCATCAGCTGC<u>AGGAGCTCCAAGAGCCTGCTGTACAAAG</u>

<u>ACGGCAAGACCTACCTGAAC</u>TGGTATTTACAGAAGCCTGGCCAGTCCCCC

CAGCTGCTGATCTAC<u>CTCATGTCCACCAGGGCC</u>TCCGGAGTGCCTGATCG

GTTCAGCGGATCCGGCAGCGGCACCGATTTCACCCTCAAGATCTCCAGGG

TGGAGGCCGAGGACGTGGGAGTGTACTATTGC<u>CAGCAGCTGGTGGAGGAC</u>

<u>CCCTTCACC</u>TTCGGCCAAGGCACAAAGCTGGAGATCAAGAGGACTGTG

The underlined parts represent CDR1, CDR2 and CDR3, with serial numbers SEQ ID NO:27-29, respectively, and the parts with no underline are FR1, FR2, FR3 and FR4 with serial numbers SEQ ID NO:30-33, respectively.

Accordingly, the amino acid sequence of light chain variable region is:

(SEQ ID NO: 34)
DIVMTQSPLSLPVTPGEPASISC<u>RSSKSLLYKDGKTYLN</u>WYLQKPGQSPQ
LLIY<u>LMSTRAS</u>GVPDRFSGSGSGTDFTLKISRVEAEDVGVYYC<u>QQLVEDP
FTF</u>GQGTKLEIKRTV

The underlined parts represent CDR1, CDR2 and CDR3, with serial numbers SEQ ID NO:35-37, respectively, and the parts with no underline are FR1, FR2, FR3 and FR4 with serial numbers SEQ ID NO:38-41, respectively.

Embodiment 3: Construction of Humanized Antibody Expression Plasmid

Using P3.1GS-hup01-HC and P3.1GS-hup01-LC as templates, the heavy and light chain fragments of full-length antibody are expanded by PCR to construct humanized antibody expression plasmid.

The upstream and downstream primers for light and heavy chains, reaction systems and PCR conditions are shown in Table 5, table 6 and table 7, respectively.

TABLE 5

Upstream and downstream primers of PCR reaction for light and heavy chain of humanized antibody

| Primer | Sequence |
|---|---|
| Heavy chain upstream | 5'GGGGTACCGCCGCCACCATGGAGACAGACACACTC CTGCTATGGGTACTGCTGCTCTGGGTTCCAGGTTCCA CTGGTGAGGTGCAACTGGTGGAAAG 3' (SEQ ID NO: 42) |
| Heavy chain downstream | 5'GGCTCTAGATCATTTTCCGAGGGACAGGG 3' (SEQ ID NO: 43) |
| Light chain upstream | 5'GGGGTACCGCCGCCACCATGGAGACAGACACACTC CTGCTATGGGTACTGCTGCTCTGGGTTCCAGGTTCCA CTGGTGACATCGTGATGACCCAGTC 3' (SEQ ID NO: 44) |
| Light chain downstream | 5' GGCTCTAGATTAACACTCTCCCCTGTTGAAGC 3' (SEQ ID NO:) |

TABLE 6

PCR reaction system for light and heavy chain of humanized antibody

| Reagent name | Volume added |
|---|---|
| Heavy/light chain template | 1 μL |
| 5x Buffer | 10 μL |
| 2.5 μM dNTP Mix | 4 μL |
| Upstream and downstream primers (10 μM) | 1 μL for each |
| Taq | 0.5 μL |
| ddH$_2$O | up to 50 μL |

TABLE 7

PCR reaction conditions for light and heavy chain of humanized antibody

| Temperature | Time | |
|---|---|---|
| 94° C. | 5 min | |
| 94° C. | 30 s | Totally 30 cycles |
| 50° C. | 30 s | |
| 72° C. | 1 min 45 s | |
| 72° C. | 7 min | |
| Cool to 4° C. | | |

The full-length sequences of light and heavy chains are recovered by PCR product recovery kit. The light chain, heavy chain and plasmid of the antibody fragment are digested by double enzyme digestion. The antibody and plasmid enzyme digestion fragments after electrophoresis are recovered by gel digestion, then linked by enzyme. The humanized antibody expression plasmid after enzyme linking is named as P3.1GS-PD-1. The reaction systems are as shown in Tables 8-10.

TABLE 8

Double enzyme digestion reaction systems for light chain and heavy chain of humanized antibody

| Reagent name | Volume added |
|---|---|
| Fragment | 22 μL |
| Buffer | 3 μL |
| Kpnl | 1.5 μL |
| Xba 1 | 1.5 μL |
| ddH$_2$O | Up to 30 μL |
| 37° C. water bath overnight | |

TABLE 9

Double enzyme digestion reaction system of expression plasmid

| Reagent name | Volume added |
|---|---|
| Plasmid pcDNA3.1GS | 1 μL |
| Buffer | 2 μL |
| Kpnl | 1 μL |
| Xba 1 | 1 μL |
| ddH$_2$O | Up to 20 μL |
| 37° C. water bath overnight | |

TABLE 10

Enzyme linked reaction system of antibody fragments and expression plasmid fragments

| Reagent name | Volume added |
|---|---|
| Plasmid fragment | 1 μL |
| Light chain/heavy chain fragment | 4 μL |
| Solution I | 5 μL |
| Reaction at 16° C. for 1 h | |

Adding the enzyme linking product to 100 μL XL1-10 competent cells and place it on ice for 30 minutes. Then heat it at 42° C. for 90 seconds, and place it on ice rapidly for 2 minutes. Next add 500 μL, LB medium, culture at 37° C. for 1 hour in shaker, centrifuge at 4000 rpm for 5 minutes and remove 500 μL supernatant, and then spray on LB solid plate containing 50 μg/mL AMP by gun blowing the suspension, and culture at 37° C. overnight. Add single colonies into 5 mL LB liquid medium (50 μg/mL AMP) and culture for 6 hours at 37° C., 250 rpm. Verify the clones by PCR, and preserve the positive strains with 15% sterilized glycerol. Each clone is prepared with 2 copies, one stored in a tube for sequencing, and the other preserved at −20° C.

Embodiment 4: Construction of Stable Cell Lines

The humanized antibody expression plasmid P3.1GS-PD-1 is linearized by PvuI before transfection, and the linearized plasmid containing humanized antibody light and heavy chain genes is transfected into CHO-KSM4 by electrotransfection for 4 times. The transfected cells are named as 20150703T, 20150704T, 20150708T and 20150714T, respectively.

After transfection, glutamine is withdrawn for pressurized screening, and the transfected cells 20150708T and 20150714T are recovered for 2 days and then laid on the plate. After culturing for 30-40 days, growth of clones can be observed in the 96-well plate, when the yield is verified. High-yield clones are transferred and expanded for culturing. When the quantity of cells reaches about 2×10$^6$ cells/mL, they are inoculated, fed and cultured in batches. After culturing, the supernatant is harvested for yield verification, to obtain the alternative parent clones. Parent clones of 20150703T and 20150704T are obtained by screening through semisolid plating method. Carry out subclonal screening on the high-yield clones: 3000-5000 cells per well are arranged on a 6-well plate through semisolid plating, with 2.5 mL medium. After plating, place at 37° C. and 5% CO2 for static culture 7-12 days, after which select monoclonal clones. The selected clones are verified for yield to obtain alternative clones.

High-yield cell lines are obtained by feeding and screening. The feeding scheme by flask shaking is as follows: CDM4CHO-based medium is used to inoculate, with the density of inoculation of 5×10$^5$ cells/mL, and the inoculated cells are cultured at 37° C., 5% CO2 and 120 rpm. The day starting the inoculation is marked as Day 0. And 70 g/L cell Boost 5 is supplemented on Day 3. The supplemented volume per day is 6% of the inoculation volume until the cells are harvested. According to the results of feeding and screening, PCB is established by choosing the cell lines with relatively high yield in different transfections, and the stability of subculture is studied. The expressed antibody is named as anti-PD-1.

Embodiment 5: Comparison of Binding Specificity and Binding Kinetics of Antibodies Biacore is used to analyze the affinity and binding kinetics of the antibody expressed in cell line 4. Using standard amine coupling chemistry and the kit provided by Biacore, the goat anti-human IgG is covalently linked to CMS chip by primary amine. Make the antibody flow in the HBS EP buffer at a flow rate of 30 L/min and measure the binding. The binding time is 300 seconds, and the dissociation time is 7200 seconds. The measured values ka, kd and KD are shown in Table 11.

TABLE 11

Binding kinetics results of humanized antibody anti-PD-1

| Sample | ka (1/Ms) | kd (1/s) | KD (M) |
|---|---|---|---|
| anti-PD-1 | $4.567 \times 10^4$ | $1.926 \times 10^{-5}$ | $4.218 \times 10^{-10}$ |

Embodiment 6: Antibody Effect on Cytokine Secretion in Mixed Lymphocyte Reaction Dilute the blood with PBS buffer at 1:1, move 3 mL LSM into the centrifugal tube, and add 4 mL diluted blood. When adding, ensure that the diluted blood to the upper layer of LSM, without mixing. RT centrifuge at 400 g for 30-40 min. Finally, extract the separated PBMC from the upper layer and centrifuge at 100 g for 10 min. Separate CD4+ T-cells by using BD's CD4+ cell separation magnetic beads, and separate DC cells by using BD's DC-cell separation magnetic beads. On the 96-well plate, the quantity of CD4+ T-cells is $1 \times 10^5$ per well; the quantity of DC is $1 \times 10^4$; and the total volume is 100 μL for co-culture. Add gradient-diluted antibody and culture for 5 days so as to test the concentrations of IFN-γ, IL-2.

Figure 9:
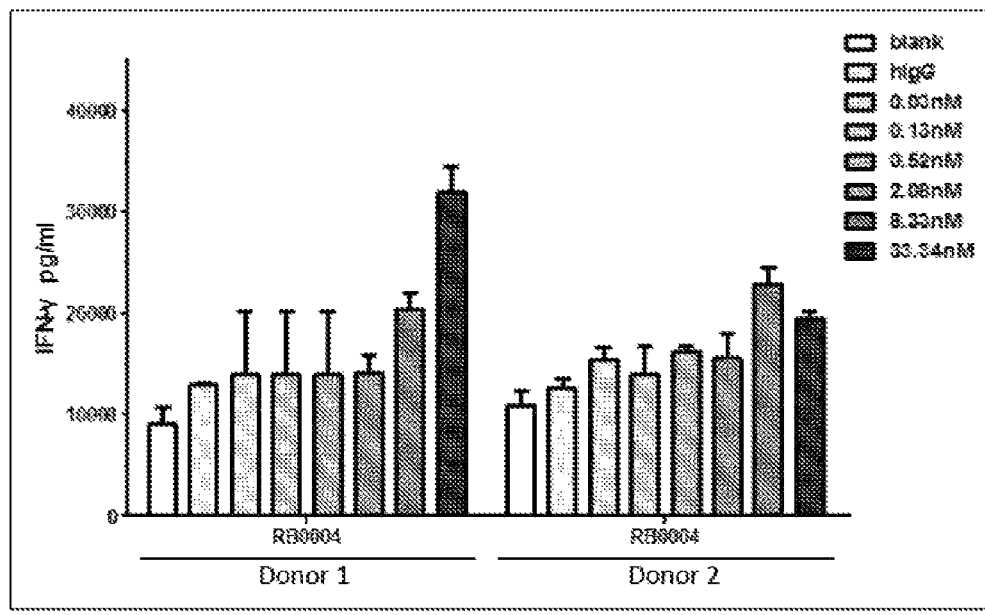
FIG. 9 shows the effect of humanized PD-1 antibody on cytokine IFN-γ secretion in mixed lymphocyte reaction.
Figure 10:
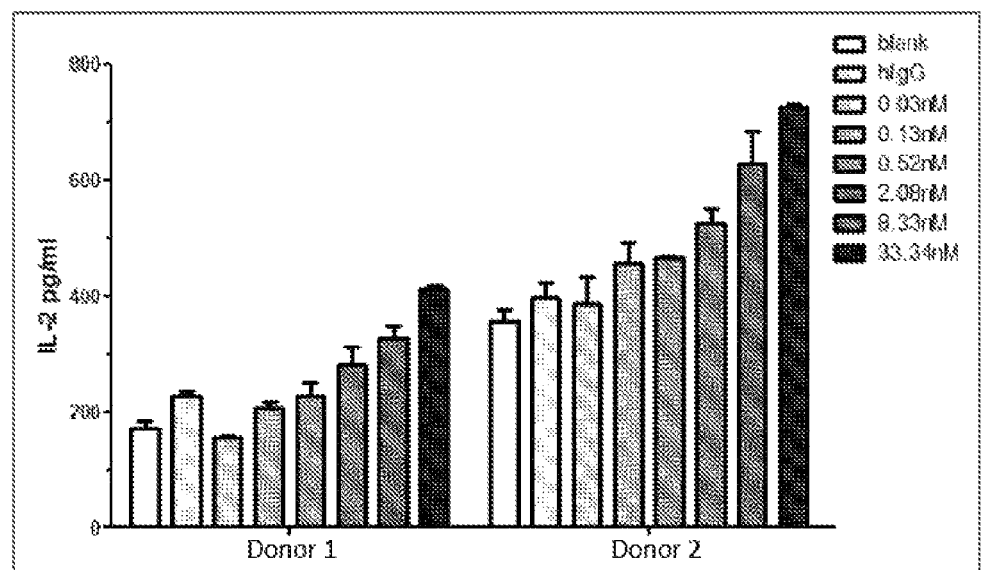
FIG. 10 shows the effect of humanized PD-1 antibody on cytokine IL-2 secretion in mixed lymphocyte reaction.

With results as shown in FIGS. 9 and 10, antibodies can effectively promote the secretion of IFN-γ and IL-2 by mixed lymphocytes.

Embodiment 7 Stability of Antibody in Serum

Dilute the humanized antibody anti-PD-1 with monkey serum, at a concentration of 0.5 mg/mL. Place it at 37° C., for 0, 1, 4 and 7 days, respectively.

Recombinant human PD-1 fusion protein is stored at 0.5 μg/mL in enveloping buffer at 4° C. overnight. Remove the solution in wells the next day and wash with PBST for twice. Then add 1% BSA, seal at 37° C. for 1 hour, then wash with PBST for twice. The stable antibody samples are diluted three folds starting from 1 μg/mL for 8 concentration gradients, incubated at 37° C. for 1 hour, and washed with PBST for three times. Dilute with goat anti-human FAB-HRP at ratio of 1:10000, incubate for 1 hour at 37 C, and wash with PBST for three times. Add TMB for 15 min coloration, stop the reaction with 0.5M $H_2SO_4$ and read out the absorbance at 450 nm.

Figure 11:
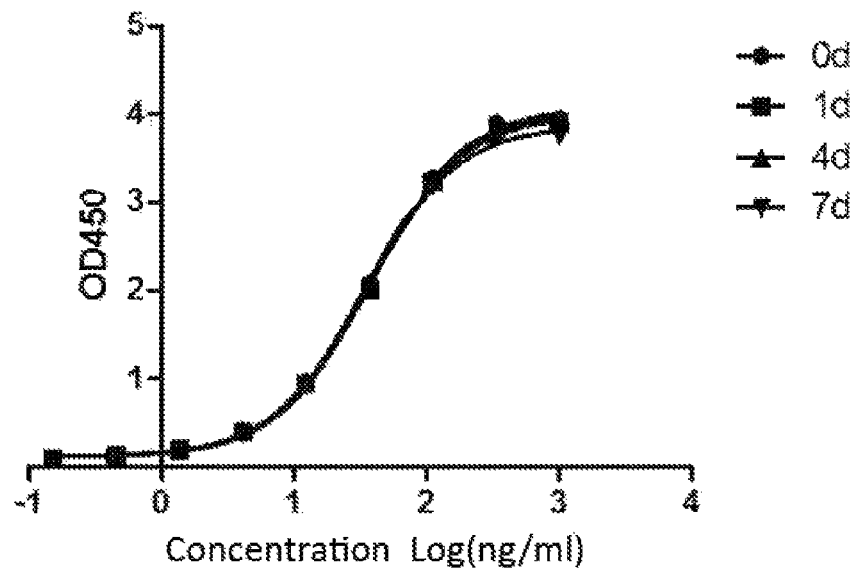
FIG. 11 shows the stability result of humanized PD-1 antibody in serum.

With results as shown in FIG. 11, the humanized antibody anti-PD-1 shows good serum stability, without significant activity attenuation within 7 days.

Embodiment 8: ELISA Assay and its Binding Specificity to Human CD28 & CTLA-4 and Binding to PD-1 Proteins of Different Species The binding of recombinant human CD28, recombinant human CTLA-4, recombinant mouse PD-1, recombinant M.fascicularis PD-1 and recombinant human PD-1 protein in recombinant CD28 family to antibodies is tested. Different proteins are stored at 0.5 μg/mL in enveloping buffer at 4° C. overnight. Remove the solution in wells the next day and wash with PBST for twice. Then add 1% BSA, seal at 37° C. for 1 hour, then wash with PBST for twice. Add 0.5 μg/mL antibody samples, incubate for 1 hour, and wash with PBST for three times. Dilute with goat anti-human FAB-HRP at ratio of 1:10000, incubate for 1 hour at 37 C, and wash with PBST for three times. Add TMB for 15 min coloration, stop the reaction with 0.5M H2SO4 and read out the absorbance at 450 nm.

Figure 12:
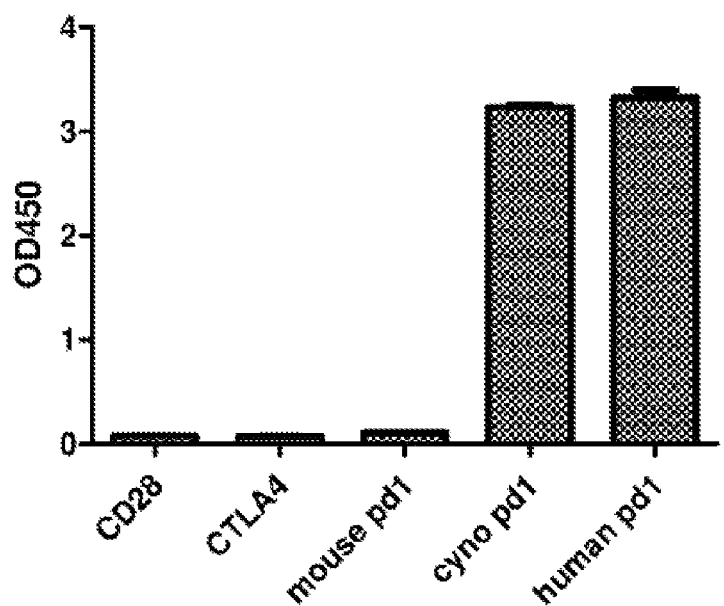
FIG. 12 shows the binding specificity of humanized PD-1 antibody to human CD28 and CTLA-4, and the binding results of humanized PD-1 antibody to PD-1 proteins of different species.

With results as shown in FIG. 12, the antibody does not bind to other members of CD28 family. The antibody binds to human and M.fascicularis recombinant PD-1 protein with similar affinity.

The preceding is simply a preferred embodiment of the present invention and is not intended to limit the invention. It should be pointed out that, for those with ordinary skills in the art, a number of improvements and variations can be made without departing from the technical principles of the invention, and these improvements and variations should also be regarded as being in the protection scope of the invention.

What is claimed is:

1. An anti-human PD-1 humanized monoclonal antibody or an antigen binding part thereof comprising the following CDR regions: a sequence of heavy chain CDR1 is shown as SEQ ID NO: 17, a sequence of heavy chain CDR2 is shown as SEQ ID NO: 18, a sequence of heavy chain CDR3 is shown as SEQ ID NO: 19, a sequence of light chain CDR1 is shown as SEQ ID NO: 35, a sequence of light chain CDR2 is shown as SEQ ID NO: 36, and a sequence of light chain CDR3 is shown as SEQ ID NO: 37.

2. The anti-human PD-1 humanized monoclonal antibody or its the antigen binding part thereof as described in claim 1 further comprising sequences selected from the following framework regions of heavy chain variable region: FR1, FR2, FR3 and FR4, as shown in SEQ ID NO: 20-23, respectively, and other sequences having greater than 70%, 80%, 85%, 90%, 95%, 99% identity to them, respectively.

3. The anti-human PD-1 humanized monoclonal antibody or its the antigen binding part thereof as described in claim 2, wherein the sequence of heavy chain is as shown in SEQ ID NO: 8.

4. The anti-human PD-1 humanized monoclonal antibody or its the antigen binding part thereof as described in claim 1 further comprising sequences selected from the following framework regions of light chain variable region: FR1, FR2, FR3 and FR4, as shown in SEQ ID NO: 38-41, respectively, and other sequences having greater than 70%, 80%, 85%, 90%, 95%, 99% identity to them, respectively.

5. The anti-human PD-1 humanized monoclonal antibody or its the antigen binding part thereof as described in claim 4, wherein the sequence of light chain is as shown in SEQ ID NO: 25.

6. A nucleic acid molecule containing a nucleic acid sequence that is capable of encoding the anti-human PD-1 humanized monoclonal antibody or its antigen binding part as described in claim 1.

7. A nucleic acid molecule as described in claim 6, wherein the heavy chain variable region of the anti-human PD-1 humanized monoclonal antibody or its antigen binding part comprises the amino acid sequence of SEQ ID NO: 16.

8. A nucleic acid molecule as described in claim 6, wherein the light chain variable region of the anti-human PD-1 humanized monoclonal antibody or its antigen binding part comprises the amino acid sequence of SEQ ID NO: 34.

9. A carrier containing the nucleic acid molecule as described in claim 6.

10. A host cell containing the nucleic acid molecule as described in claim 6 or a carrier that contains the nucleic acid molecule.

11. A conjugate containing the anti-human PD-1 humanized monoclonal antibody or the antigen binding part thereof as described in claim 1, and other bioactive substances, wherein the anti-human PD-1 humanized monoclonal antibody or the antigen binding part is directly or through junction fragments, coupled with other bioactive substances.

12. A composition containing the anti-human PD-1 humanized monoclonal antibody or its the antigen binding part thereof as described in claim 1, as well as optional pharmaceutically acceptable carriers or excipients, and optional other bioactive substances.

13. A method of treating tumors or T-cell dysfunction comprising administering, to a patient in need thereof, a therapeutically effective amount of the anti-human PD-1 humanized monoclonal antibody or the antigen binding part thereof as described in claim 1.

14. A carrier containing the nucleic acid molecule as described in claim 8.

15. A host cell containing the nucleic acid molecule as described in claim 8 or a carrier that contains the nucleic acid molecule.

16. A composition containing the nucleic acid molecule as described in claim 6 or a carrier that contains the nucleic acid molecule or a host cell that contains the nucleic acid molecule or a host cell that contains the carrier, as well as optional pharmaceutically acceptable carriers or excipients, and optional other bioactive substances.

17. A composition containing the nucleic acid molecule as described in claim 8 or a carrier that contains the nucleic acid molecule or a host cell that contains the nucleic acid molecule or a host cell that contains the carrier, as well as optional pharmaceutically acceptable carriers or excipients, and optional other bioactive substances.

18. A composition containing the conjugate as described in claim 11, as well as optional pharmaceutically acceptable carriers or excipients, and optional other bioactive substances.

19. A method of treating tumors or T-cell dysfunction comprising administering, to a patient in need thereof, a therapeutically effective amount of the nucleic acid molecule as described in claim 6 or a carrier that contains the nucleic acid molecule or a host cell that contains the nucleic acid molecule or a host cell that contains the carrier.

20. A method of treating tumors or T-cell dysfunction comprising administering, to a patient in need thereof, a therapeutically effective amount of the nucleic acid molecule as described in claim 8 or a carrier that contains the nucleic acid molecule or a host cell that contains the nucleic acid molecule or a host cell that contains the carrier.

21. A method of treating tumors or T-cell dysfunction comprising administering, to a patient in need thereof, a therapeutically effective amount of the conjugate as described in claim 11.

22. A method of treating tumors or T-cell dysfunction comprising administering, to a patient in need thereof, a therapeutically effective amount of the composition as described in claim 12.

23. A method of treating tumors or T-cell dysfunction comprising administering, to a patient in need thereof, a therapeutically effective amount of the composition as described in claim 16.

24. A method of treating tumors or T-cell dysfunction comprising administering, to a patient in need thereof, a therapeutically effective amount of the composition as described in claim 17.

25. A method of treating tumors or T-cell dysfunction comprising administering, to a patient in need thereof, a therapeutically effective amount of the composition as described in claim 18.

* * * * *